US012697021B2

(12) United States Patent
Inglis et al.

(10) Patent No.: US 12,697,021 B2
(45) Date of Patent: Aug. 4, 2026

(54) VIDEO LARYNGOSCOPE AND MEDICAL DEVICE WIRELESS VIDEO TRANSFER

(71) Applicant: Covidien LP, Mansfield, MA (US)

(72) Inventors: Peter Douglas Colin Inglis, Boulder, CO (US); Derek S. Tata, Longmont, CO (US); Mark Y. Su, Boulder, CO (US)

(73) Assignee: Covidien LP, Mansfield, MA (US)

( * ) Notice: Subject to any disclaimer, the term of this patent is extended or adjusted under 35 U.S.C. 154(b) by 155 days.

(21) Appl. No.: 18/649,037

(22) Filed: Apr. 29, 2024

(65) Prior Publication Data

US 2024/0398221 A1     Dec. 5, 2024

Related U.S. Application Data

(60) Provisional application No. 63/505,275, filed on May 31, 2023.

(51) Int. Cl.
*A61B 1/267*          (2006.01)
*A61B 1/00*           (2006.01)

(52) U.S. Cl.
CPC .......... *A61B 1/267* (2013.01); *A61B 1/00013* (2013.01); *A61B 1/00016* (2013.01); *A61B 1/00039* (2013.01); *A61B 1/00045* (2013.01)

(58) Field of Classification Search
CPC ............ A61B 1/00045; A61B 1/00048; A61B 1/00009; A61B 1/00016; A61B 1/00029; A61B 1/267; A61B 1/2673; A61B 1/2676; A61B 1/2733
See application file for complete search history.

(56) References Cited

U.S. PATENT DOCUMENTS

| | | | |
|---|---|---|---|
| 8,194,122 B2 | 6/2012 | Amling et al. | |
| 8,652,033 B2 | 2/2014 | Berci et al. | |
| 8,715,172 B1 | 5/2014 | Girgis | |
| 8,746,239 B2 | 6/2014 | Yoshida | |
| 8,827,899 B2 | 9/2014 | Farr et al. | |
| 8,982,199 B2 | 3/2015 | Amling et al. | |
| 9,123,155 B2 | 9/2015 | Cunningham et al. | |

(Continued)

FOREIGN PATENT DOCUMENTS

| | | |
|---|---|---|
| EP | 2433553 A1 | 3/2012 |
| JP | 2014210085 A | 11/2014 |

(Continued)

OTHER PUBLICATIONS

Ambu_aScope_3_Large_Brochure_4963605 (Oct. 2017).

(Continued)

*Primary Examiner* — Eduardo C Robert
*Assistant Examiner* — Tara Rose E Carter

(57) ABSTRACT

A video laryngoscope system where a video laryngoscope automatically connects to one or more medical devices within a patient environment. The video laryngoscope may automatically, upon startup and without further user input, perform an unfamiliar wireless connection process for each of a plurality of external devices to establish a wireless connection to each of the plurality of external devices. The video laryngoscope may then transmit, via the established wireless connections, images captured by the video-laryngoscope camera to the plurality of external devices.

20 Claims, 10 Drawing Sheets

(56) References Cited

U.S. PATENT DOCUMENTS

| | | | |
|---|---|---|---|
| 9,498,112 | B1 | 11/2016 | Stewart et al. |
| 9,538,908 | B2 | 1/2017 | Allyn et al. |
| 9,687,141 | B2 | 6/2017 | McGrath |
| 9,820,641 | B2 | 11/2017 | McGrath |
| 10,010,379 | B1 | 7/2018 | Gibby et al. |
| 10,149,957 | B2 | 12/2018 | Runnels |
| 2007/0197896 | A1 | 8/2007 | Moll et al. |
| 2007/0236514 | A1 | 10/2007 | Agusanto et al. |
| 2008/0177146 | A1 | 7/2008 | Chen |
| 2008/0177148 | A1 | 7/2008 | Chen et al. |
| 2008/0312507 | A1 | 12/2008 | Kim |
| 2011/0130632 | A1 | 6/2011 | McGrail et al. |
| 2011/0137127 | A1 | 6/2011 | Schwartz |
| 2011/0245609 | A1 | 10/2011 | Laser |
| 2013/0057667 | A1 | 3/2013 | McGrath |
| 2013/0102253 | A1* | 4/2013 | Marsh .................... H04W 4/80 |
| | | | 455/41.2 |
| 2013/0267838 | A1 | 10/2013 | Fronk et al. |
| 2014/0031700 | A1 | 1/2014 | Ferrantelli |
| 2014/0160261 | A1 | 6/2014 | Miller et al. |
| 2014/0275760 | A1 | 9/2014 | Lee et al. |
| 2014/0378763 | A1 | 12/2014 | Atarot |
| 2015/0080655 | A1 | 3/2015 | Peterson et al. |
| 2016/0199009 | A1 | 7/2016 | Gilboa |
| 2016/0279365 | A1 | 9/2016 | Esnouf |
| 2017/0055809 | A1 | 3/2017 | Omoto |
| 2017/0209071 | A1 | 7/2017 | Zhao et al. |
| 2017/0258313 | A1 | 9/2017 | McGrath |
| 2018/0193102 | A1 | 7/2018 | Inoue |
| 2018/0292199 | A1 | 10/2018 | Tojo et al. |
| 2018/0296281 | A1 | 10/2018 | Yeung et al. |
| 2018/0324352 | A1 | 11/2018 | Furuhata |
| 2019/0133430 | A1 | 5/2019 | Inglis et al. |
| 2020/0029793 | A1 | 1/2020 | McGrath |
| 2020/0121199 | A1 | 4/2020 | Freeman |
| 2020/0195903 | A1 | 6/2020 | Komp et al. |
| 2020/0275824 | A1 | 9/2020 | Tata |
| 2020/0367742 | A1 | 11/2020 | McGrath |
| 2020/0383561 | A1 | 12/2020 | McGrath |
| 2021/0052140 | A1 | 2/2021 | Tata |
| 2021/0121155 | A1 | 4/2021 | Maguire |
| 2021/0127949 | A1 | 5/2021 | Tata |
| 2021/0128033 | A1 | 5/2021 | Tata |
| 2021/0137350 | A1 | 5/2021 | Inglis |
| 2021/0257856 | A1 | 8/2021 | Ng |
| 2021/0259536 | A1 | 8/2021 | Inglis |
| 2021/0275008 | A1 | 9/2021 | McGrath |
| 2021/0318382 | A1 | 10/2021 | McGrath |
| 2022/0104694 | A1* | 4/2022 | Shelton, IV ........ G06F 3/04845 |
| 2022/0110504 | A1* | 4/2022 | Inglis ................. A61B 1/00016 |
| 2022/0225859 | A1 | 7/2022 | Phillips |
| 2022/0257092 | A1 | 8/2022 | Ng |
| 2022/0354380 | A1 | 11/2022 | Tata |
| 2023/0029630 | A1 | 2/2023 | Ng |
| 2023/0124693 | A1 | 4/2023 | Jagelski |

FOREIGN PATENT DOCUMENTS

| | | | | |
|---|---|---|---|---|
| WO | WO-2005113374 | A2 * | 12/2005 | ............. A61B 1/041 |
| WO | WO-2016042503 | A1 * | 3/2016 | ........... A61B 5/1032 |
| WO | 2020/005890 | A1 | 1/2020 | |
| WO | 2021/084061 | | 5/2021 | |
| WO | 2022/041107 | | 3/2022 | |
| WO | 2023/067523 | A1 | 4/2023 | |

OTHER PUBLICATIONS

Mcgrath Mac—Video Laryngoscope Operator's Manual Instructions for Use—Aircraft Medical Ltd (2017) www.aircraftmedical. com—23 pages.

Siena, Francesco Luke, et al.; "The development of a novel steerable bougie to assist in airway management," Austrasian Medical Journal, 2016, vol. 9, No. 5, pp. 124-137. http://dx.doi.org/10.4066/AMJ.2016.2619.

Sowers, Nicholas, et al.; "Use of a flexible intubating scope in combination with a channeled video laryngoscope for managing a difficult airway in the emergency department," The Journal of Emergency Medicine, 2016, vol. 52, No. 2, pp. 315-319.http://dx. doi.org/10.1016/j.jermermed.2015.10.010.

Weissbrod, Philip A., et al.; "Reducing injury during video-assisted endotracheal intubation: The "smart stylet" concept," The Laryngoscope, Nov. 2011, vol. 121, pp. 2391-2393.

Rothfield, Kenneth; "The video laryngoscopy market: Past, present, and future," Anesthesiology News Guide to Airway Management, 2014, pp. 29-34.

Lee, Hyung-Chul, "Real-time endoscopic image orientation correction system using an accelerometer and gyrosensor," Plos One | https://doi.org/10.1371/journal.pone.0186691 (Nov. 3, 2017).

International Search Report for International Application No. PCT/IB2024/055098 mailed Jul. 25, 2024 (17 pages).

* cited by examiner

Room 2

Room 1

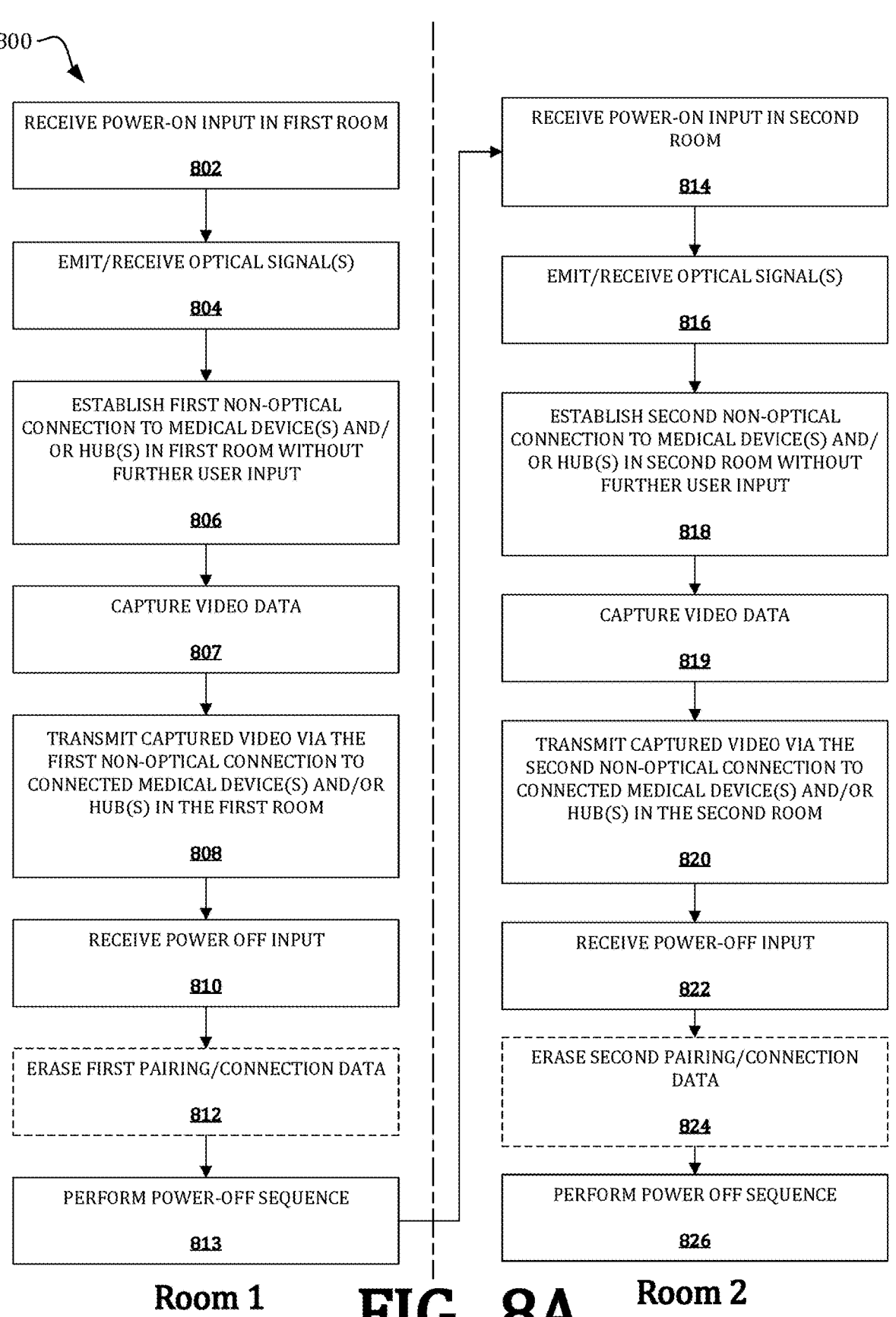
Room 1     FIG. 8A     Room 2

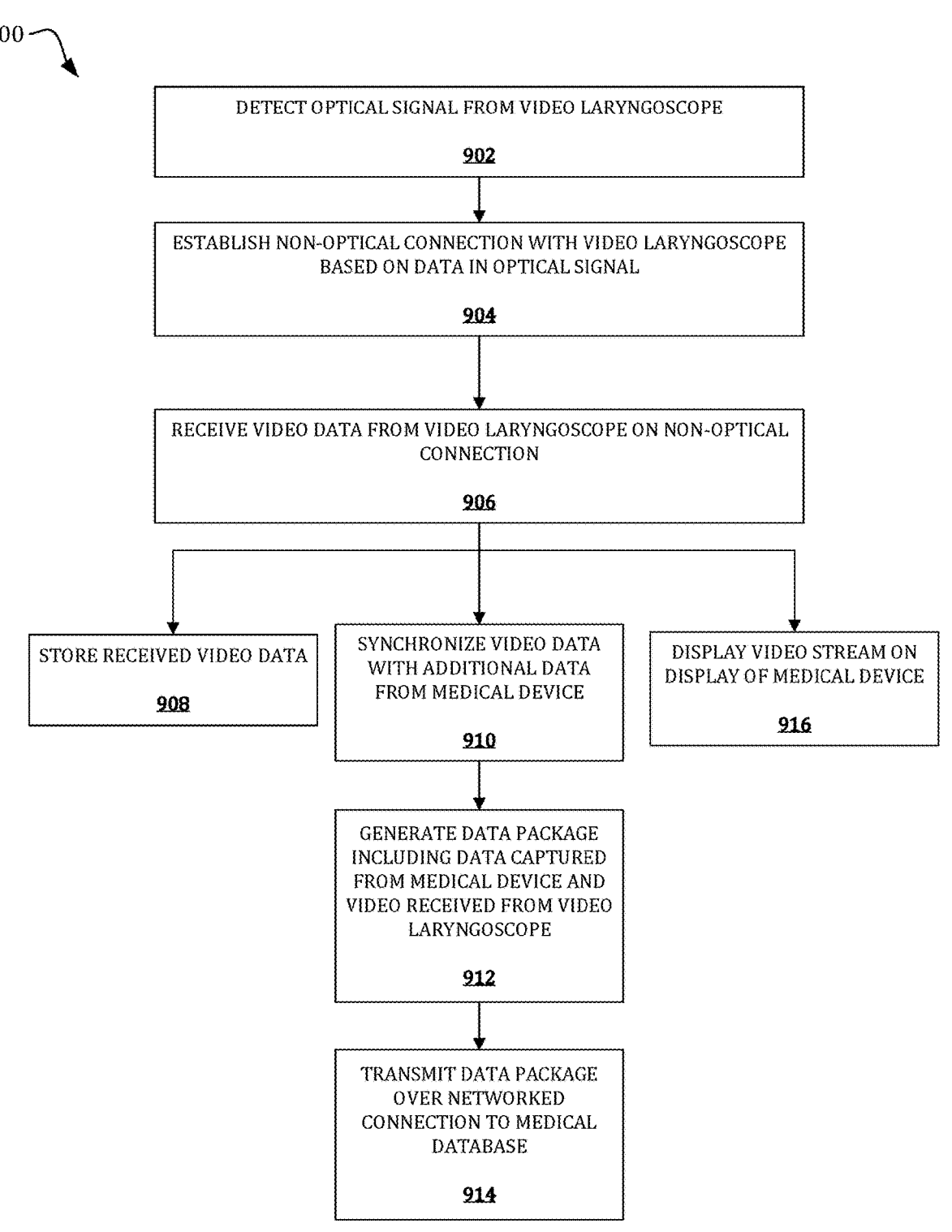

900

DETECT OPTICAL SIGNAL FROM VIDEO LARYNGOSCOPE

902

ESTABLISH NON-OPTICAL CONNECTION WITH VIDEO LARYNGOSCOPE BASED ON DATA IN OPTICAL SIGNAL

904

RECEIVE VIDEO DATA FROM VIDEO LARYNGOSCOPE ON NON-OPTICAL CONNECTION

906

STORE RECEIVED VIDEO DATA

908

SYNCHRONIZE VIDEO DATA WITH ADDITIONAL DATA FROM MEDICAL DEVICE

910

DISPLAY VIDEO STREAM ON DISPLAY OF MEDICAL DEVICE

916

GENERATE DATA PACKAGE INCLUDING DATA CAPTURED FROM MEDICAL DEVICE AND VIDEO RECEIVED FROM VIDEO LARYNGOSCOPE

912

TRANSMIT DATA PACKAGE OVER NETWORKED CONNECTION TO MEDICAL DATABASE

VIDEO LARYNGOSCOPE AND MEDICAL DEVICE WIRELESS VIDEO TRANSFER

CROSS REFERENCE TO RELATED APPLICATION

The present application claims the benefit of U.S. Provisional Patent Application Ser. No. 63/505,275, filed on May 31, 2023, the entire content of which is incorporated herein by reference.

BACKGROUND

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Laryngoscopes are commonly used during intubation (the insertion of an endotracheal tube into the trachea of a patient). A video laryngoscope is used to perform indirect laryngoscopy in which a medical professional (such as a doctor, therapist, nurse, or other practitioner) views a video image of the patient's larynx on a display screen. A video laryngoscope may include an integral display that is in the line-of-sight of the laryngoscope operator so that the patient airway is viewable on the display screen in real-time to facilitate navigation and insertion of tracheal tubes within the airway.

SUMMARY

Certain embodiments are summarized below. These embodiments are not intended to limit the scope of the disclosure. Indeed, the present disclosure may encompass a variety of forms that may be similar to or different from the embodiments set forth below.

In an aspect, the technology relates to a system for transmitting video laryngoscope images. The system includes a plurality of external devices including a medical device with a display screen; and a video laryngoscope comprising a camera, an optical transceiver, a non-optical wireless transmitter, a processor, and memory storing instructions that, when executed by the processor, cause the video laryngoscope to perform operations. The operations include automatically, upon startup and without further user input, performing an unfamiliar wireless connection process for each of the plurality of external devices to establish a wireless connection to each of the plurality of external devices; and transmitting, via the established wireless connections, images captured by the camera to the plurality of external devices.

In an example, the medical device is one a defibrillator, an anesthesia machine, a multi-parameter monitor, a medical imaging device, an electrocardiogram (ECG) machine, or an intravenous (IV) pump. In another example, the medical device displays, on the display, the images transmitted by video laryngoscope. In yet another example, performing unfamiliar wireless connection process includes: exchanging wireless signals, having a first wireless signal type, between the video laryngoscope and the each of the plurality of external devices; and wherein the wireless connection is of a second wireless signal type, and establishing the wireless connection is based on data in exchanged wireless signals. In a further example, the video laryngoscope comprises a first transceiver that communicates on the first wireless signal type and a second transceiver that communicates on the second wireless signal type; and each of the plurality of medical devices include a first transceiver that communicates on the first wireless signal type and a second transceiver that communicates on the second wireless signal type. In still another example, the wireless signals are optical signals, and the established wireless connections are non-optical connections. In still yet another example, the unfamiliar wireless connection process comprises, upon startup, emitting an optical signal that encodes identification information for the video laryngoscope.

In another example, the medical device comprises an optical window in a housing of the medical device and an optical transceiver positioned behind the optical window of the medical device. In yet another example, the plurality of external devices are physically located in a first room with the video laryngoscope, and the operations further include receiving a power-off input; powering off the video laryngoscope; receiving a power-on input in a second room adjacent the first room; based on receiving the power-on input, detecting an optical signal from a medical device in the second room; and based on the optical signal from a medical device in the second room, establishing a non-optical connection with the optical signal from a medical device in the second room but not any of the plurality of external devices located in the first room.

In another aspect, the technology relates to a system for transmitting video laryngoscope images. The system includes a medical device that includes a first optical transceiver that detects and emits optical signals; a first non-optical wireless transceiver that transmits and receives non-optical data signals; a display; a first memory; and a first processor. The system also includes a headless hub that includes a second optical transceiver that detects and emits optical signals; a second non-optical wireless transceiver that transmits and receives non-optical data signals; a second memory; and a second processor. The system further includes a video laryngoscope that includes a camera that acquires images; a third optical transceiver that detects and emits optical signals; a third non-optical wireless transceiver that transmits and receives non-optical data signals; a third processor; and a third memory storing instructions that, when executed by the third processor, causes the video laryngoscope to perform operations. The operations comprise detect, by the third optical transceiver, a first optical signal from the first optical transceiver of the medical device; detect, by the third optical transceiver, a second optical signal from the second optical transceiver of the headless hub; based on data in the first optical signal, establish, by the third non-optical wireless transceiver and without prior or further user input, a first non-optical connection with the first non-optical wireless transceiver of the medical device; based on data in the second optical signal, establish, by the third non-optical wireless transceiver and without prior or further user input, a second non-optical connection with the second non-optical wireless transceiver of the headless hub; capture, by the camera, video data; transmit the captured video data to the medical device via the first non-optical connection; and transmit the captured video data to the headless hub via the second non-optical connection.

In an example, the first memory of the medical device stores instructions that, when executed by the first processor causes the medical device to perform operations including:

receive the transmitted video data from the video laryngoscope; and display the video data on the display. In another example, the first memory of the medical device stores instructions that, when executed by the first processor causes the medical device to perform operations further including: generate physiological parameter data about a patient; combine the video data and the physiological parameter data into a data package; and transmit the data package to medical database located remotely from the medical device. In yet another example, the medical device further includes an optical window in a housing of the medical device, and the first optical transceiver is positioned behind the optical window. In still another example, the medical device further includes a video-laryngoscope pairing printed circuit board assembly (PCBA) that includes the first processor, the first memory, the first optical transceiver, and the first non-optical wireless transceiver; and a primary-function PCBA that includes a fourth processor and a fourth memory that stores instructions for performing primary functions of the medical device.

In another aspect, the technology relates to a method, performed by a video laryngoscope, for transmitting image data captured by the video laryngoscope. The method includes while in a first patient environment, receiving a first power-on input; upon startup in response to the first power-on input and without requiring any further user input, detecting a first optical signal from a first medical device having a first display screen; based on the first optical signal and without pre-pairing, establishing a first non-optical connection with the first medical device; capturing first images by a camera of the video laryngoscope during a first medical procedure being performed in the first patient environment; transmitting the first images to the first medical device via the first non-optical connection; powering off the video laryngoscope; subsequently, while in a second patient environment, receiving a second power-on input; upon startup in response to the second power-on input, and without requiring any further user input, detecting a second optical signal from a second medical device having a second display screen, the second medical device being different from the first medical device; based on the second optical signal and without pre-pairing, establishing a second non-optical connection with the second medical device and not the first medical device; capturing second images by the camera of the video laryngoscope during a second medical procedure being performed in the second patient environment; and transmitting the second images to the second medical device via the second non-optical connection.

BRIEF DESCRIPTION OF THE DRAWINGS

Advantages of the disclosed techniques may become apparent upon reading the following detailed description and upon reference to the drawings in which:

FIG. 8A depicts an example method for wirelessly connecting a video laryngoscope to medical devices in multiple rooms.

FIG. 9 depicts an example method for wirelessly receiving and processing video data received from a video laryngoscope.

DETAILED DESCRIPTION

Figure 1:
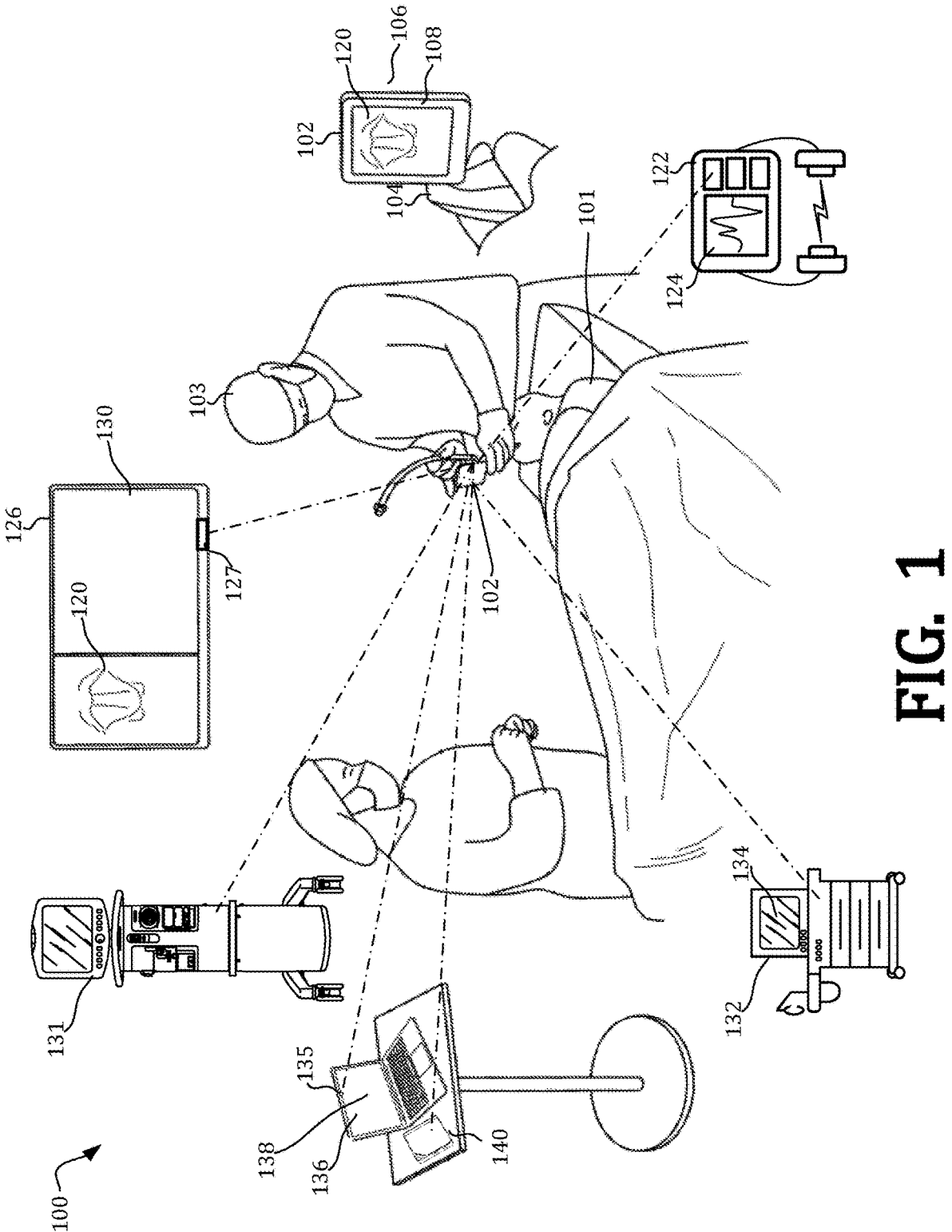
FIG. 1 depicts an example patient environment including a video laryngoscope in communication with one or more medical devices.

A medical professional may use a laryngoscope to view a patient's oral cavity to facilitate insertion of a tracheal tube (e.g., endotracheal tube, tracheostomy tube, or transtracheal tube) through the patient's oral or nasal cavity and into the patient's trachea as part of an intubation procedure. Video laryngoscopes (VLs) include a camera on a portion of the laryngoscope that is inserted into the patient's oral cavity to obtain an image (e.g., still image and/or moving image, such as a video) of the oral cavity. The image may then be displayed during the intubation procedure on a display screen of the video laryngoscope to enable the medical professional to visualize the oral cavity and to facilitate manipulation and insertion of the tracheal tube. The images acquired by the video laryngoscope can provide important context to other medical professionals participating in a medical procedure. Accordingly, in some cases, the video laryngoscope can be linked to an external display that replicates the display screen of the video laryngoscope such that other medical professionals can track the progress of the intubation or other airway procedure in real time on the external display.

In some cases, rather than each medical professional having his or her own personal device, video laryngoscopes can be a shared resource, e.g., provided from a hospital or other medical inventory, for use during a medical procedure. After the procedure is complete, the video laryngoscope can be cleaned and returned to the inventory for maintenance and storage until needed again. As a result, over the course of several different medical procedures, a particular video laryngoscope can be used by different medical professional to acquire videos and/or still images during medical procedures with different patients and in different locations. In addition, the video laryngoscope can include recording capabilities such that images of each individual procedure can be saved directly to a memory of the video laryngoscope. While video laryngoscopes can directly store acquired images, accessing the images from the memory of the video laryngoscope may not be convenient for medical professionals wishing to review their past procedures.

The presently disclosed technology helps alleviate the above issues, among others, by providing for medical devices that can communicate directly with the video laryngoscope and receive the video data captured by the video laryngoscope. Video laryngoscopes are often used in environments that also include other medical devices. For instance, a video laryngoscope may be used in emergency situations (e.g., in an ambulance) where devices such as defibrillators are present. As another example, the video laryngoscope may be used in a hospital setting where an anesthesia machine is present and adjacent to the patient.

The presently disclosed technology enables the medical devices (e.g., defibrillator, anesthesia machine) to include technology that allows for automatic connection to the video laryngoscope without any input (other than a power-on input) from the user. As a result, the video data captured from the video laryngoscope may be transmitted to the medical device(s) for display and/or storage. By enabling the medical devices themselves to automatically connect and communicate with the video laryngoscope, no additional external devices are required to be used or attached to such medical devices to relay the video data from the video laryngoscope. Such an advantage can be particularly useful in emergency situations where connection or installation of a separate device is not possible, or at least not desirable, as such a process could further delay life-saving treatment.

As briefly mentioned above, pairing of the video laryngoscope and the medical device may also be automatically and securely performed with limited to no input by the user of the video laryngoscope. The video laryngoscope may also not store or use any prior unique connection information for the medical devices(s) to which the video laryngoscope connects. Such processes may be referred to as an unfamiliar wireless connection process. As an example, in an embodiment when the video laryngoscope is powered on, the video laryngoscope automatically emits an optical signal to indicate its availability to pair with the medical device. The medical device then optically communicates data to the video laryngoscope for pairing. Authentication and/or pairing data is then exchanged, via the optical frequency, between the medical device and the video laryngoscope to facilitate pairing over a more robust non-optical wireless communication band, such as a WiFi or Bluetooth connection. Once the non-optical wireless communication connection is established between the video laryngoscope and the medical device, video data is then transmitted from the video laryngoscope to the medical device via the non-optical wireless communication connection. In some examples, the pairing process begins automatically with the powering on of the video laryngoscope when it is within the same room or environment as the medical device.

By using the optical signal to establish the pairing, additional layers of security are provided in the process. For example, because the optical signal needs a line-of-sight (or reflection) between the two devices, there is an added assurance that the video laryngoscope and the medical device are within the same room. Further, unlike other pairing methods that require user input (e.g., entering a matching code), the present pairing method requires no additional user input to complete the pairing, even without previously pairing the medical device to the laryngoscope or storing any information about the pairing. The video laryngoscope connect automatically even to unfamiliar devices the first time they communicate with each other, which allows the medical professional to immediately focus on the medical procedure rather than the pairing process.

FIG. 1 depicts a schematic illustration of an example patient environment 100 including a video laryngoscope 102 in communication with one or more medical devices. The patient environment 100 can be any room or theater where an intubation is being performed, such as a medical suite in a hospital or other care setting, an operating or other procedure room, patient recovery room, an emergency intubation setting (e.g., an ambulance), or other environments.

A laryngoscope operator 103 holds a handle 104 of the video laryngoscope 102, where the handle 104 is coupled to a display 106 having a display screen 108. Acquired images 120 are displayed on the display screen 108. The video laryngoscope 102 may be used as part of an intubation procedure to advance an endotracheal tube into the airway of a patient 101 to secure the airway for mechanical ventilation. Accordingly, the operator 103 of the video laryngoscope 102 performs the intubation and directly manipulates the endotracheal tube within the patient's airway, and other clinicians in the patient environment assist the laryngoscope operator 103, monitor the condition of the patient, prepare or adjust medical equipment in the patient environment, and/or wait until the airway is secured to perform other procedures or interventions. As provided herein, the images 120 can be stored in a memory on the video laryngoscope 102. The images 120 acquired by the video laryngoscope 102 are visible on the laryngoscope display screen 108. The images 120 may be in the form of video data (e.g., a video feed, video stream).

The patient environment 100 may include a plurality of devices including medical devices, computing devices, external displays, and/or headless hubs, among other devices. In the example depicted, the patient environment includes two example medical devices in the form of a defibrillator 122, with a defibrillator display 124, and a ventilator 131 or anesthesia machine 132 with an anesthesia display 134. The patient environment 100 may include additional or alternative medical devices, such as medical devices from medical device original equipment manufacturers (OEMs). For example, the additional or alternative medical devices may include patient monitors (e.g., pulse oximeters, blood pressure monitor), multi-parameter patient monitors, medical imaging equipment, electrocardiogram (ECG) machines, an intravenous (IV) pump, and the like. The multi-parameter patient monitor may include, or be connected to, sensors for measuring physiological parameters of the patient during the intubation procedure, such as pulse oximetry sensors, heart rate sensors, ECG, sensors, and/or blood pressure sensors.

The example patient environment 100 also includes an external display 126 that includes an external display screen 130 where images may be displayed. For instance, as depicted in FIG. 1, a portion of the display screen 130 may display the images 120 from the video laryngoscope 102 when the video laryngoscope 102 is connected to the external display screen 126. The example patient environment 100 may further include a computer 136, which may be a laptop or other type of computing device, that includes a computer display screen 138. A wireless, headless hub 140 may also be present in the example patient environment 100. The headless hub 140 may be headless, meaning that it operates without a dedicated or integrated display and/or user interface. One example of a wireless hub is described in U.S. patent application Ser. No. 18/047,481, which is incorporated herein by reference in its entirety. To the extent the discussion in the present application conflicts with the material in the incorporated reference, the discussion in the present application shall control.

In an embodiment, the video laryngoscope 102 wirelessly connects to any of the devices in the example patient environment 100 discussed above. Once connected to one or more of the respective devices, the video laryngoscope 102 transmits video data to the respective devices, where the receiving device may display and/or store the received video data.

As described in further detail below, connection or pairing of the video laryngoscope 102 with the various devices in the example patient environment 100 may be performed through the use of optical and non-optical signals with little to no input required from the laryngoscope operator 103 or other clinical staff. In an embodiment, when the video laryngoscope 102 is powered on (e.g., in response to a manual selection of a power button), the video laryngoscope 102 goes through an initial pairing process that includes the emission of an optical signal that is received by one or more of the devices in the example patient environment 100. For instance, an optical transceiver of the video laryngoscope 102 emits an optical signal through an optically transparent window of the video laryngoscope 102 such that the optical signal is emitted throughout the example patient environment 100. The other device(s) then detect the optical signal from the video laryngoscope 102. For example, the defibrillator 122 may also include an optical transceiver within the housing of the defibrillator 122. The optical transceiver of the defibrillator 122 processes the received optical signal from the video laryngoscope 102, and the defibrillator 122 then emits an optical response signal of its own via its optical transceiver. The video laryngoscope 102 receives this optical response signal, and a non-optical connection between the video laryngoscope 102 and defibrillator 122 may then be established.

Once the non-optical connection is established between the video laryngoscope 102 and the other device, the video data captured by the video laryngoscope 102, such as the images 120, are transmitted by the video laryngoscope to the other device via the non-optical connection. Once received by the device, the video data (e.g., images 120) may be displayed and/or stored by the device. For example, the defibrillator 122 may display the images 120 on the defibrillator display 124. Additionally or alternatively, the defibrillator 122 may store the images 120 in memory of the defibrillator 122 such that the images 120 may be accessed at a later time after the intubation procedure has been completed.

In an embodiment, the defibrillator 122 (or other medical device) is connected to another computing device, either via a wireless or wired connection, and the stored images 120 are transmitted from the defibrillator 122 to the other computing device or database. In some examples, the defibrillator 122 (or other medical device) has a network connection to another device or database that is remote from the defibrillator 122, such as in another room of the hospital or offsite from the hospital. For instance, the database may be a medical database for storing electronic medical records (EMRs).

The medical device(s) may also capture additional data about the patient or procedures being performed. For instance, physiological parameters of the patient may be monitored, sensed, measured, etc. by the medical device. Usage or operational data of the medical device may also be generated. This additional data may be synchronized with the video data from the video laryngoscope 102 in some examples, and/or the additional data may be packaged with the video data to form an enriched data package that includes data generated from the medical device as well as the video data received from the video laryngoscope 102. This data package can be stored on the medical device or transmitted to another database such as a hospital EMR.

While the defibrillator 122 is referred to above, other devices may operate in a similar manner. For example, once a connection between the anesthesia machine 132 and the video laryngoscope 102 is established, images 120 from the video laryngoscope 102 may be displayed on the anesthesia display 132. Once a connection is established between the external display 126 and the video laryngoscope 102, the images 120 received from the video laryngoscope 102 may be displayed on the external display screen 130. For instance, the acquired images 120 from the video laryngoscope 102 are streamed from the video laryngoscope 102 to the external display 126 for display on all or a portion of an external display screen 130. Thus, in an embodiment, the images 120 displayed on the laryngoscope display screen 108 and streamed to the external display screen 130 are substantially the same real-time images. When a connection is established between the computer 136 and the video laryngoscope 102, the images 120 may be displayed on the computer display screen 138 and/or stored in memory of the computer 136. When a connection is established between the wireless hub 140 and the video laryngoscope 102, the wireless hub 140 may store but not display the received images 120 because the wireless hub 140 does not include a display. In other examples, the wireless hub 140 may be connected to an additional external display and further transmit the images 120 to that display. The connections between the video laryngoscope 102 and the various devices in the patient environment 100 may occur concurrently such that video data may be transmitted concurrently to multiple devices during the intubation procedure.

While the wireless hub 140 is shown in FIG. 1 as positioned on a table, in other examples the wireless hub may be positioned in different locations and/or additional wireless hubs may be present in the patient environment 100. For instance, the wireless hubs may be worn on lanyards, clipped to a gown, etc. by different medical professionals participating in the medical procedure and who wish to receive the images 120.

As described herein, the pairing or connection process includes an initial exchange of data in the form of optical signals. Accordingly, each of the devices may have one or more optical windows that are at least partially transparent in the spectrum for which the optical signal is transmitted (e.g., infrared). For instance, the video laryngoscope 102, the anesthesia machine 132 and the defibrillator 122 may have optical windows through which the optical signals may pass. An optical transceiver internal to the device and behind the window may then convert the optical signal into an electric data signal that can be processed by the device.

The optical transceivers discussed herein may be in the form of a transmitter and/or a receiver that may be packaged together or separately. In some examples, the medical devices may include a transmitter or a receiver or a transceiver. The transceiver may emit a signal, e.g., an infrared or other wavelength optical signal, to the video laryngoscope 102. The transceiver may also receive optical signals. The transceiver can be carried by, e.g., positioned in or on, the housing of the medical devices.

In some examples, the transceiver is positioned at an edge or corner of the housings of the medical devices to facilitate multidirectional transmission and/or receipt of an initiating first signal for pairing to the video laryngoscope 102. The medical devices may also include an additional or separate transmitter or transceiver, e.g. a second transmitter or transceiver, that communicates using a second non-optical signal.

By using the optical signal to initiate pairing, connections are limited to devices that are in direct or indirect line-of-sight of the video laryngoscope 102. Such line-of-sight optical transmission avoids undesired pairing between devices and video laryngoscopes 102 in different, adjacent rooms. For example, unlike other wireless signals, such as WiFi or Bluetooth signals, optical signals cannot pass through walls. Accordingly, by using an optical signal to initiate pairing, additional security is added that the video laryngoscope 102 and any device to which the video laryngoscope 102 pairs are in the same room. In addition, in medical environments, many of the surfaces are optically reflective. Thus, a direct line of sight between the video laryngoscope 102 and the medical device may not be necessary as the optical signal may reflect off other surfaces already present in the operating room. While the reflections may enable different positions of the medical devices relative to the video laryngoscope 102, the use of the optical signal still ensures that the video laryngoscope 102 and the medical devices are in same room.

After line-of-sight pairing is initiated via the optical signals, completion of the pairing or connection, and subsequent communication, is conducted using a more robust communication technique, such as non-optical wireless communication, that does not rely on line-of-sight transmission. Thus, temporary disruption of line-of-sight between the medical device and the video laryngoscope will not interrupt communication between the medical device and the video laryngoscope 102 after the pairing is established.

Figure 2:
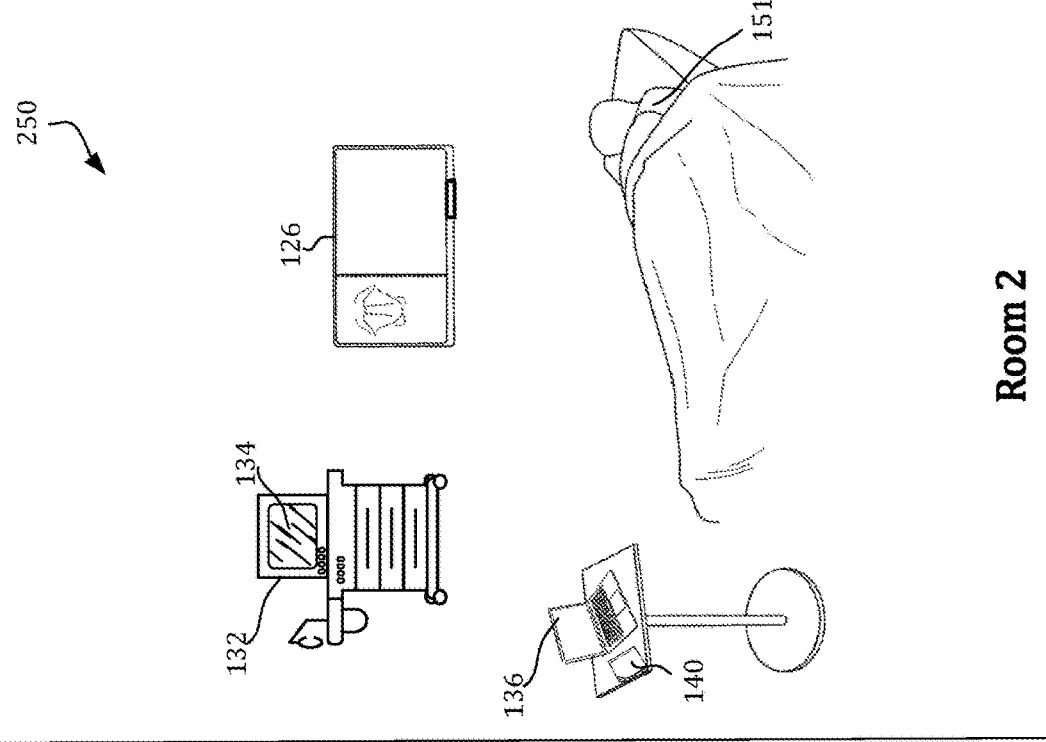
FIG. 2 depicts an example view of two rooms or patient environments with a video laryngoscope in use in the first room.
Figure 2:
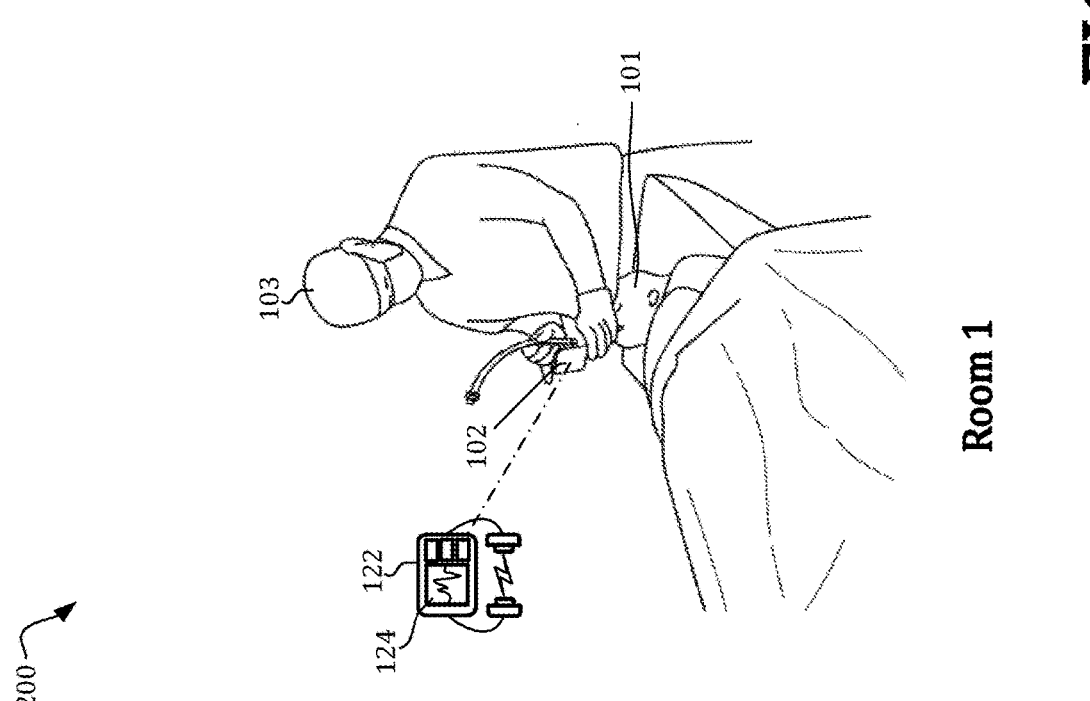

FIG. 2 depicts a view of two example rooms or patient environments with a video laryngoscope 102 in use in the first room 200. Within in the first room 200, which may be an emergency scenario such as in an ambulance, a defibrillator 122 is present. When the laryngoscope operator 103 begins the intubation procedure on the patient 101, the laryngoscope operator 103 powers on the video laryngoscope 102. Upon powering on the video laryngoscope 102, the video laryngoscope 102 automatically pairs to the defibrillator 122 without the need for additional input from the laryngoscope operator 103, even if the video laryngoscope 102 and defibrillator 122 have never before been paired or communicated or exchanged information. For instance, the laryngoscope operator 103 does not need to enter any additional pairing codes or maneuver through any menus on the video laryngoscope 102. Instead, the laryngoscope operator 103 may immediately start using the video laryngoscope 102 for the medical procedure, and the transmission of the video data to the connected defibrillator 122 begins automatically after powering on the laryngoscope.

The defibrillator 122 may store the received video data for later analysis, such as after the intubation procedure has been completed and the patient is in a stable condition. In some examples, the defibrillator 122 may display the images from the video data on the defibrillator display 124. As such, other medical professionals within the first room 200 may be able to see the images captured by the video laryngoscope 102 in substantially real time.

When the intubation procedure is completed and the video laryngoscope 102 is powered off, the pairing or connection information for the defibrillator 122 is automatically erased or removed from memory of the defibrillator 122 to prevent future connection to the video laryngoscope 102 without repeating the optical pairing process discussed herein. In some examples, the video laryngoscope 102 is moved to a second room 250 where another medical procedure is performed, as discussed next.

Figure 3:
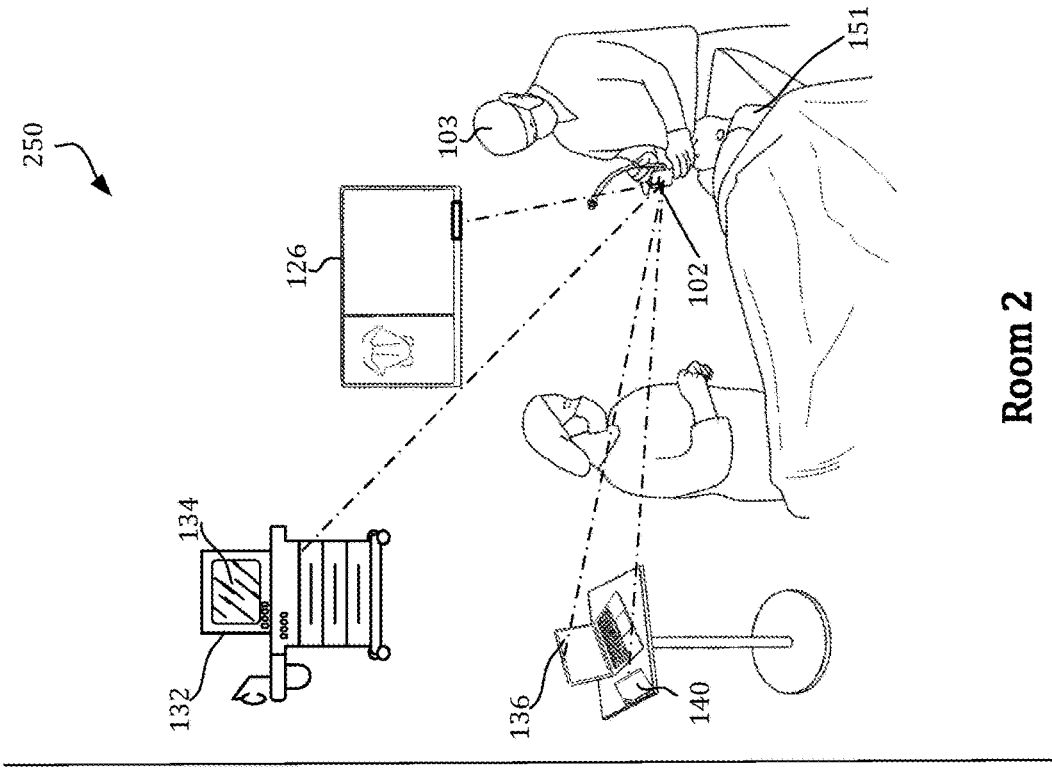
FIG. 3 depicts an example view of the two rooms of FIG. 2 with the video laryngoscope in use in the second room.
Figure 3:
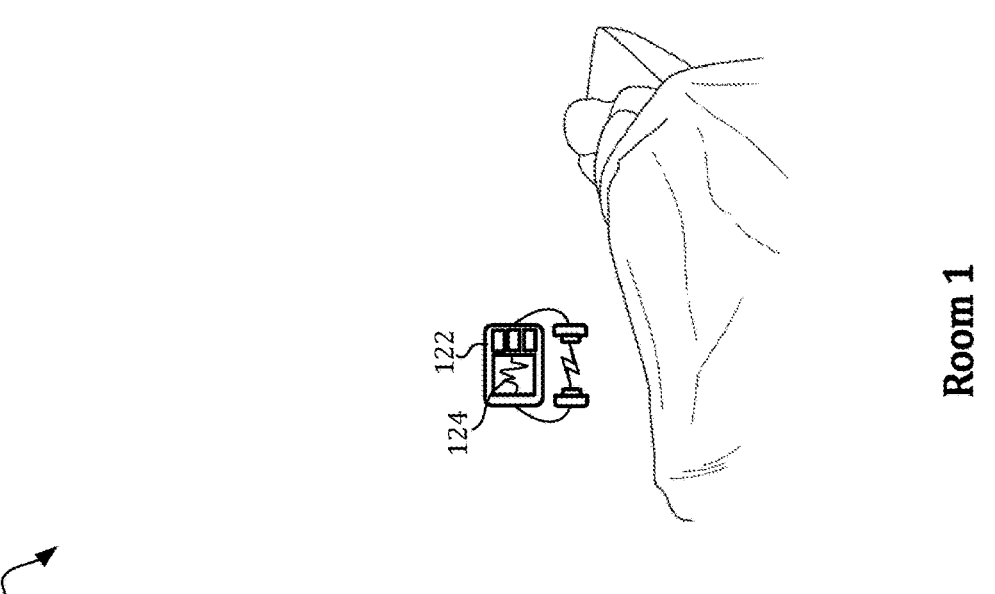

FIG. 3 depicts the example view of the two rooms of FIG. 2 with the video laryngoscope 102 in use in the second room 250 for an intubation procedure of a second patient 151. In FIG. 3, the same video laryngoscope 102 is now in second room 250, which may be separated by a wall from the first room 200. The second room 250 includes different devices than the first room 200. For instance, the second room 250 may include one or more different medical devices, such as an anesthesia machine 132. The second room 250 may also include an external display screen 126, a computer 136, and a headless hub 140.

When the video laryngoscope 102 is powered on in the second room 250, the video laryngoscope 102 automatically connects to at least one of the anesthesia machine 132, external display screen 126, computer 136, and/or headless hub 140 via the optical pairing process described herein. Once connected or paired, the video data from the video laryngoscope 102 is transmitted to the connected devices over the non-optical connection.

Of note, while the video laryngoscope 102 may still be in the non-optical connection range of the defibrillator 122 in room 200, the video laryngoscope 102 does not pair with the defibrillator 122. Unlike other devices that retain connection data (e.g., Bluetooth, Wifi) and automatically reconnect upon startup, the video laryngoscope 102 does not perform such functions. For instance, the video laryngoscope 102 does not access or utilize prior connection data to reestablish connections with devices to which it has previously connected. FIG. 3 provides a good example of why such reconnection is prevented. If the video laryngoscope 102 was to reconnect to the defibrillator 122 in room 200 while the video laryngoscope 102 was being used in room 250 for a different patient, the video data received by the defibrillator 122 would be for the wrong patient and potential cause confusion or mislabeling of the resultant video data.

Figure 4:
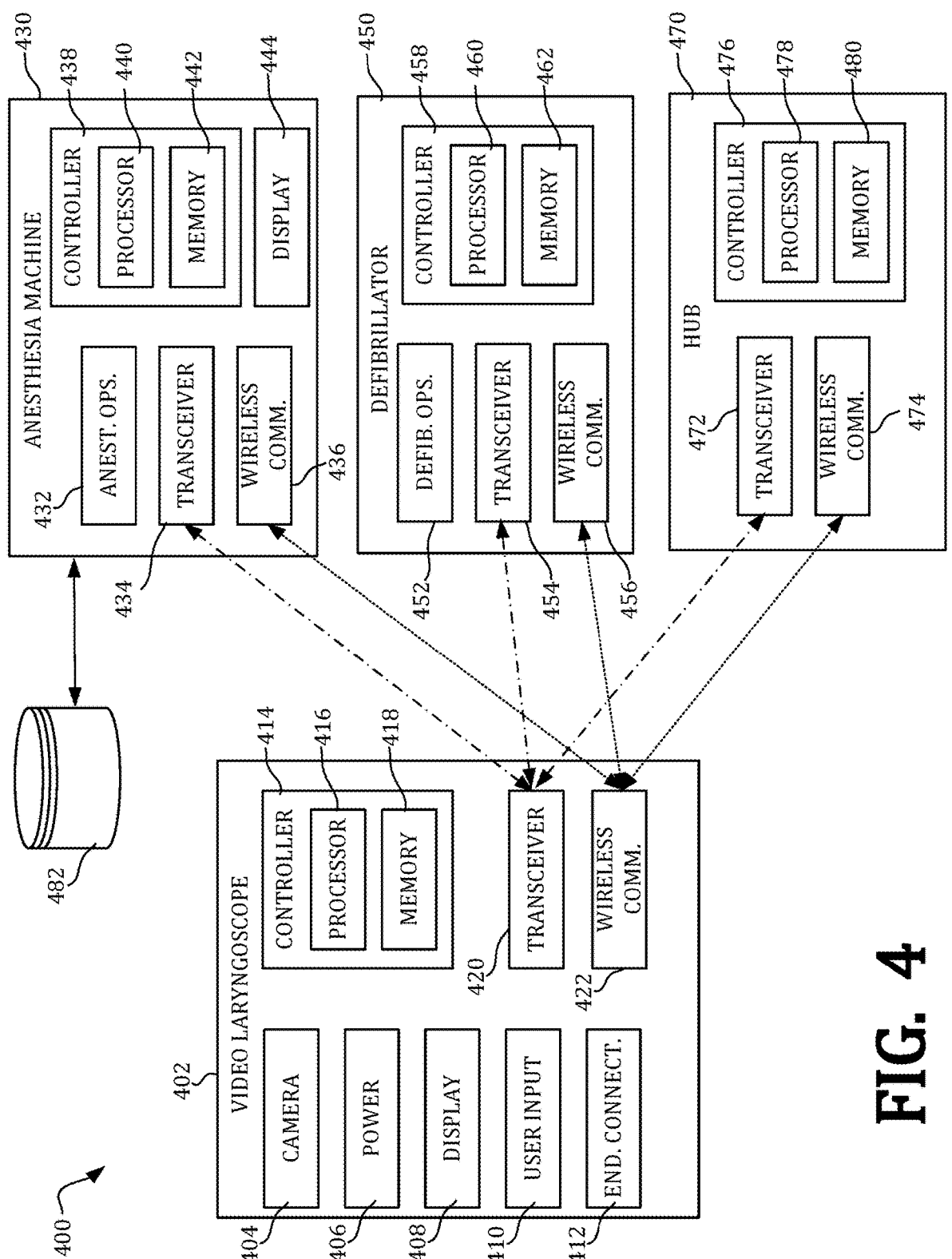
FIG. 4 depicts an example schematic diagram of a video laryngoscope in communication with multiple medical devices and a headless hub.

FIG. 4 depicts an example schematic diagram of an imaging system 400 that includes a video laryngoscope 402 in communication with multiple medical devices 430, 450 and a headless hub 470. The two example medical devices are an anesthesia machine 430 and a defibrillator 450.

The video laryngoscope 402 includes a camera 404, a power source 406 (e.g., battery), a display 408, user inputs 410 (e.g., touch sensor, power button), an endoscope connector 412, and an electronic controller 414 that includes one or more processors 416 and hardware memory 418. The video laryngoscope 402 can provide indicators of wireless pairing via the display 408, as well as other indicators, such as haptic, audio, and/or other visual indicators.

The video laryngoscope 402 receives or captures images from the camera 404. The video laryngoscope 402 may also receive images captured by an external endoscope camera that is connected to the video laryngoscope 402 via the endoscope port 412. The images from the camera 404 and/or the external endoscope camera may be transmitted to the other devices discussed herein.

The video laryngoscope 402 also includes an optical transceiver 420 (such as an infrared detector and/or transmitter) for transmitting and receiving the optical signals discussed herein. The video laryngoscope 402 further includes a wireless communication device 422. The wireless communication device 422 may be a wireless transceiver that is configured to establish wireless communication in a non-optical frequency. By way of example, the wireless communication device 422 may be configured to communicate using the IEEE 802.15.4 standard, and may communicate, for example, using ZigBee, WirelessHART, or MiWi protocols. Additionally or alternatively, the wireless communication devices 422, 436, 456, 474 may be configured to communicate using the Bluetooth standard or one or more of the IEEE 802.11 standards or similar communication techniques.

The anesthesia machine 430 includes primary anesthesia operation components 432 that provide the primary functions of the anesthesia machine 430. For instance, the anesthesia operation components 432 may include components such as a gas supply, vaporizer, inspiratory and expiratory ports, flow and pressures sensors, etc. The anesthesia machine 430 also includes an electronic controller 438 with one or more processors 440 and hardware memory 442. The anesthesia machine 430 may also include a display 444.

The anesthesia machine 430 further includes an optical transceiver 434 (such as an infrared detector and/or transmitter) that exchanges optical signals with the transceiver 420 of the video laryngoscope 402. A wireless communication device 436 is also included in the anesthesia machine 430. The wireless communication device 436 may be similar to, or the same as, the wireless communication device 422 of the video laryngoscope 102 in that the wireless communication device 436 may operate according to one or more of the communications protocols described above. Following establishment of the non-optical pairing, the video data from the video laryngoscope 402 is received by the wireless communication device 436.

The anesthesia machine 430 may also be in communication with a medical database 482 such as a hospital EMR. The medical database may store patient records or other information received from one or more medical devices, such as the anesthesia machine 430. When the anesthesia machine 430 receives the video data from the video laryngoscope 402, the anesthesia machine 430 may also transmit the video data to the medical database 482. In some examples, the video data is further enhanced or packaged with additional data captured by the anesthesia machine 430. The packaged data may then be transmitted to the medical database 482. While only the anesthesia machine 430 is depicted as communicating with the database 482, other medical devices may also communicate with the database 482.

The defibrillator 450 includes primary defibrillator operation components 452 that provide the primary functions of the defibrillator 450. The defibrillator operation components 452 may include components such as a discharge generator or source (e.g., capacitor), paddles, electrodes, ECG monitor, etc. The defibrillator 450 also includes a controller 458 with one or more processors 460 and hardware memory 462.

The defibrillator 450 further includes an optical transceiver 454 (such as an infrared detector and/or transmitter) that exchanges optical signals with the transceiver 420 of the video laryngoscope 402. A wireless communication device 456 is also included in the defibrillator 450. The wireless communication device 456 may be similar to, or the same as, the wireless communication device 422 of the video laryngoscope 102. Following establishment of non-optical pairing, the video data from the video laryngoscope 402 is received by the wireless communication device 456.

The headless hub 470 includes an electronic controller 476 with one or more processors 478 and hardware memory 480. The hub 470 further includes an optical transceiver 472 (such as an infrared detector and/or transmitter) that exchanges optical signals with the transceiver 420 of the video laryngoscope 402. A wireless communication device 474 is also included in the hub 470. The wireless communication device 474 may be similar to, or the same as, the wireless communication device 422 of the video laryngoscope 102. Following establishment of non-optical pairing, the video data from the video laryngoscope 402 is received by the wireless communication device 474.

The hardware memory 418, 442, 462, 480 may include a volatile memory, such as random access memory (RAM), and/or a nonvolatile memory, such as read-only memory (ROM). For example, the memory 418, 442, 462, 480 may store processor-executable instructions (e.g., firmware or software) for the processors 416, 440, 460, 478 to execute. The hardware memory 418, 442, 462, 480 may store images 120 and instructions (e.g., software or firmware for storing the images, transmitting the images, etc.), and any other suitable data. The processors 416, 440, 460, 478 may be microprocessors, microcontrollers, central processing units (CPUs), etc. Generally, the processors 416, 440, 460, 478 are electronic devices or integrated circuitry that execute a set of instructions to perform various computational and data processing tasks.

The video laryngoscope 402 may also connect to some external devices, such as the external display screen and the computer, that may already include at least an optical receiver. The optical data signals discussed herein may be received by that optical receiver. For instance, an external display screen may include an optical window that allows optical signals to pass, such as optical signals from a traditional remote control for the external display. The present technology may utilize that pre-existing optical technology of the display to receive and process the optical signals discussed herein. Similarly, a computer may include a pre-existing camera that may serve as an optical receiver or detector. The camera may be used to detect and process the optical signals discussed herein. In some examples, the computer may include a separate infrared receiver and optical window. While these devices may include an optical receiver, an optical transmitter may still need to be incorporated within the devices. The optical transmitter, however, may be positioned behind the pre-existing optical window for those particular devices.

Figure 5:
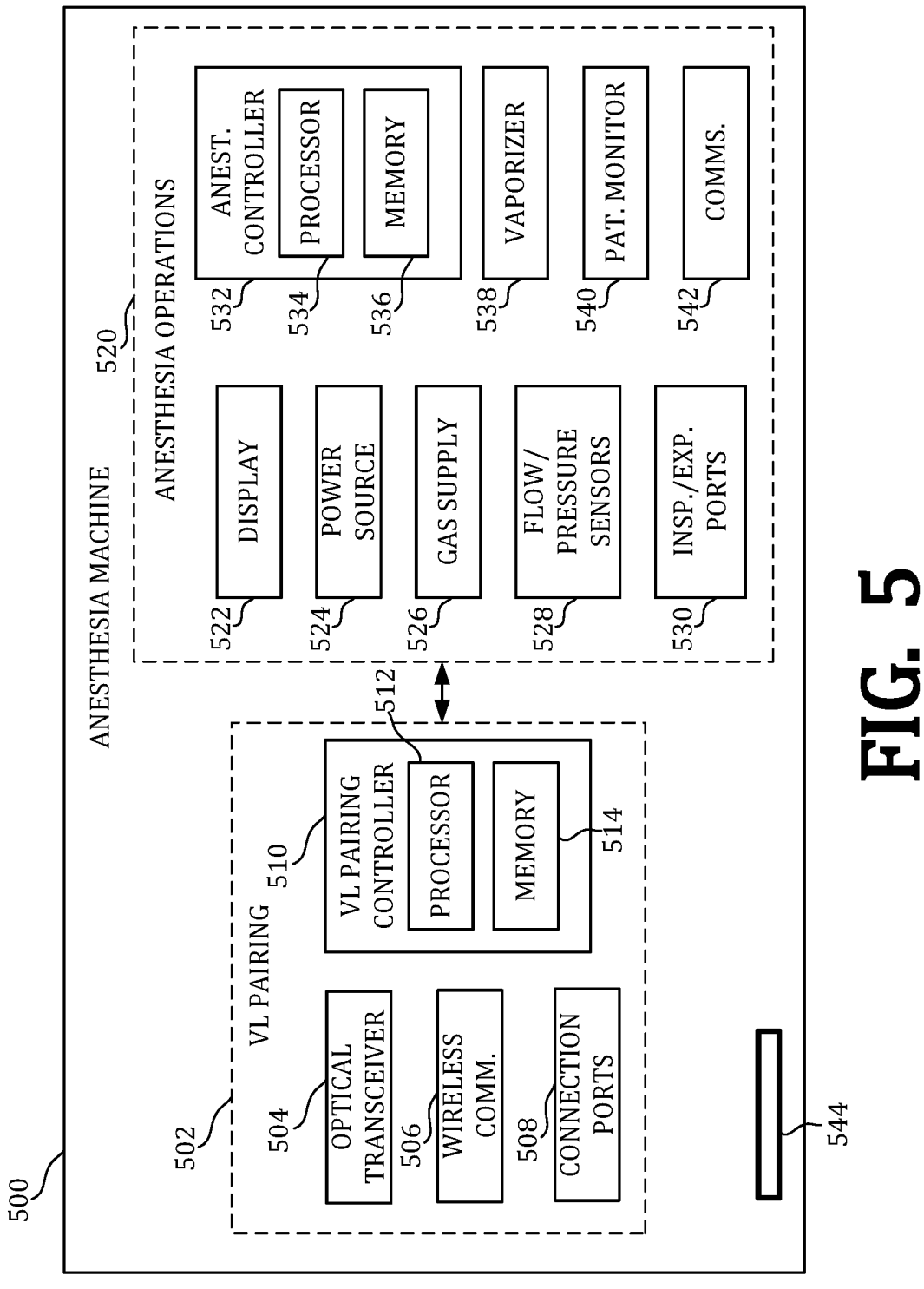
FIG. 5 depicts a schematic diagram of an example anesthesia machine.

FIG. 5 depicts a schematic diagram of an example anesthesia machine 500. The example anesthesia machine 500 includes a pairing section 502 and an anesthesia operations section 520. The components of the pairing section 502 may be positioned on, or connected to, a first circuit board or a first set of circuit boards (e.g., printed circuit board assembly (PCBA)), and the components of the anesthesia operations section 520 may be positioned on, or connected to, a second circuit board or second set of circuit boards. In examples, the hardware and/or circuitry of the pairing section 502 is integrated and/or non-removable from the medical device. For instance, the components and/or circuit boards may be physically attached inside the housing of the medical device via screws, adhesives, solder, or other attachment means. The components are non-removable in that they are not intended to be removed or detached by a user (with the limited exception of for repair or replacement during maintenance of the medical device). In the example depicted, the hardware and/or circuitry of the pairing section 502 are not included in any type of removable dongle, plug, or other type or removable or detachable component. The hardware and/or circuitry of the anesthesia operations section 520 are similarly integrated and non-removable from the medical device.

The pairing section 502 includes an optical transceiver 504, a wireless communications device 506 for non-optical communication, and one or more connection ports 508 to interface with the components of the anesthesia operations section 520. The anesthesia machine 500 may also include an optical window 544 formed in the housing of the anesthesia machine 500 to allow for the optical signals to reach the optical transceiver 504 and exit the anesthesia machine 500. The optical transceiver 504 and the wireless communications device 506 may be the same or similar as the corresponding devices described and depicted in FIG. 4.

The pairing section 502 also includes a pairing controller 510 that includes one or more processors 512 and hardware memory 514. The processor(s) 512 and memory 514 control the pairing process with the video laryngoscope but may not control the anesthesia operations of the anesthesia machine 500.

The anesthesia operations section 520 includes a display 522, a power source 524, a gas supply 526, flow and/or pressure sensors 528, inspiratory and/or expiratory ports and valves 530, a vaporizer 538, and/or patient monitoring components 540. The anesthesia operations section 520 also includes an anesthesia controller 532 that includes one or more processors 534 and hardware memory 536. The anesthesia controller 532 controls the anesthesia operations but may not control or perform operations relating to the pairing of the anesthesia machine 500 with a video laryngoscope. The anesthesia operations section 520 also includes communication device(s) 542 for communicating with devices other than the video laryngoscope. For instance, the communication device(s) 542 may provide for Internet or other networked communications, such as to a medical database or monitoring station.

By having some duplicate components (e.g., processors, memory, communication devices), the primary functions of the anesthesia machine 500 may be segregated from the pairing functions. As such, any operations relating to pairing are less likely to potentially interfere with the life-saving operations of the anesthesia machine 500. However, in other examples (such as in FIG. 4), only a single set of processors, memory, and/or communication devices may be present in the anesthesia machine 500 that control both the pairing operations and the anesthesia operations. Such examples reduce the need for duplicate hardware, which ultimately conserves resources and provides for more efficient medical devices.

Figure 6:
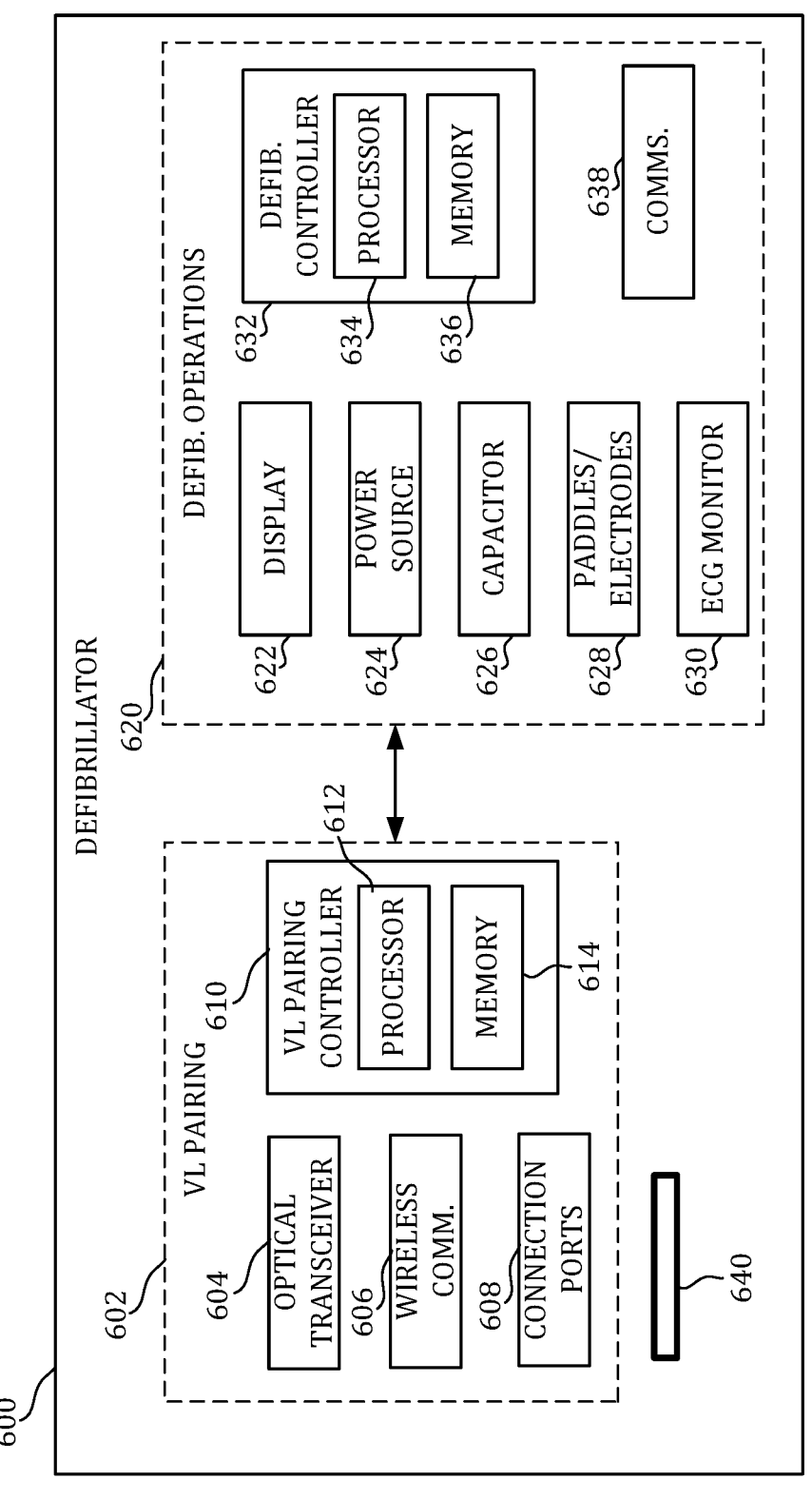
FIG. 6 depicts a schematic diagram of an example defibrillator.

FIG. 6 depicts a schematic diagram of an example defibrillator 600. The example defibrillator 600 includes a pairing section 602 and a defibrillator operations section 620. The components of the pairing section 602 may be positioned on, or connected to, a first circuit board or a first set of circuit boards (e.g., PCBA), and the components of the defibrillator operations section 620 may be positioned on, or connected to, a second circuit board or second set of circuit boards.

The pairing section 602 may be substantially similar to the pairing section 502 discussed above with respect to the anesthesia machine 500. For instance, the pairing section 602 includes an optical transceiver 604, a wireless communications device 606 for non-optical communication, and one or more connection ports 608 to interface with the components of the defibrillator operations section 620. The defibrillator 600 may also include an optical window 640 formed in the housing of the defibrillator 600 to allow for the optical signals to reach the optical transceiver 504 and exit the defibrillator 600. The optical transceiver 604 and the wireless communications device 606 may be the same or similar as the corresponding devices described and depicted in FIG. 4. The hardware and/or circuitry of the pairing section 602 can be integrated in multiple different medical devices to enable the same video laryngoscope to connect to and stream video files to these different medical devices, without customized pairing or configuration of the video laryngoscope to enable that pairing. For instance, the set of hardware and/or circuitry of the pairing section 602 may be integrated into a different medical device other than the defibrillator 600 and operate to allow for pairing of that different medical device. In some examples, the set of hardware and/or circuitry (e.g., PCBA) of the pairing section may be incorporated into multiple different medical devices.

The pairing section 602 also includes a pairing controller 610 that includes one or more processors 612 and hardware memory 514. The processor(s) 612 and memory 614 control the pairing process with the video laryngoscope but may not control the defibrillator operations of the defibrillator 600.

The defibrillator operations section 620 may include a display 622, a power source 624, a discharge source (e.g., capacitor 626), paddles and/or electrodes 628, and/or an ECG monitor 630. The defibrillator operations section 620 also includes a defibrillation controller 632 that includes one or more processors 634 and hardware memory 636. The defibrillation controller 632 controls the defibrillation operations but may not control or perform operations relating to the pairing of the defibrillator 600 to the video laryngoscope. The defibrillator operations section 620 may also include communication device(s) 638 for communicating with devices other than the video laryngoscope. For instance, the communication device(s) 542 may provide for Internet or other networked communications, such as to a medical database or monitoring station.

Figure 7:
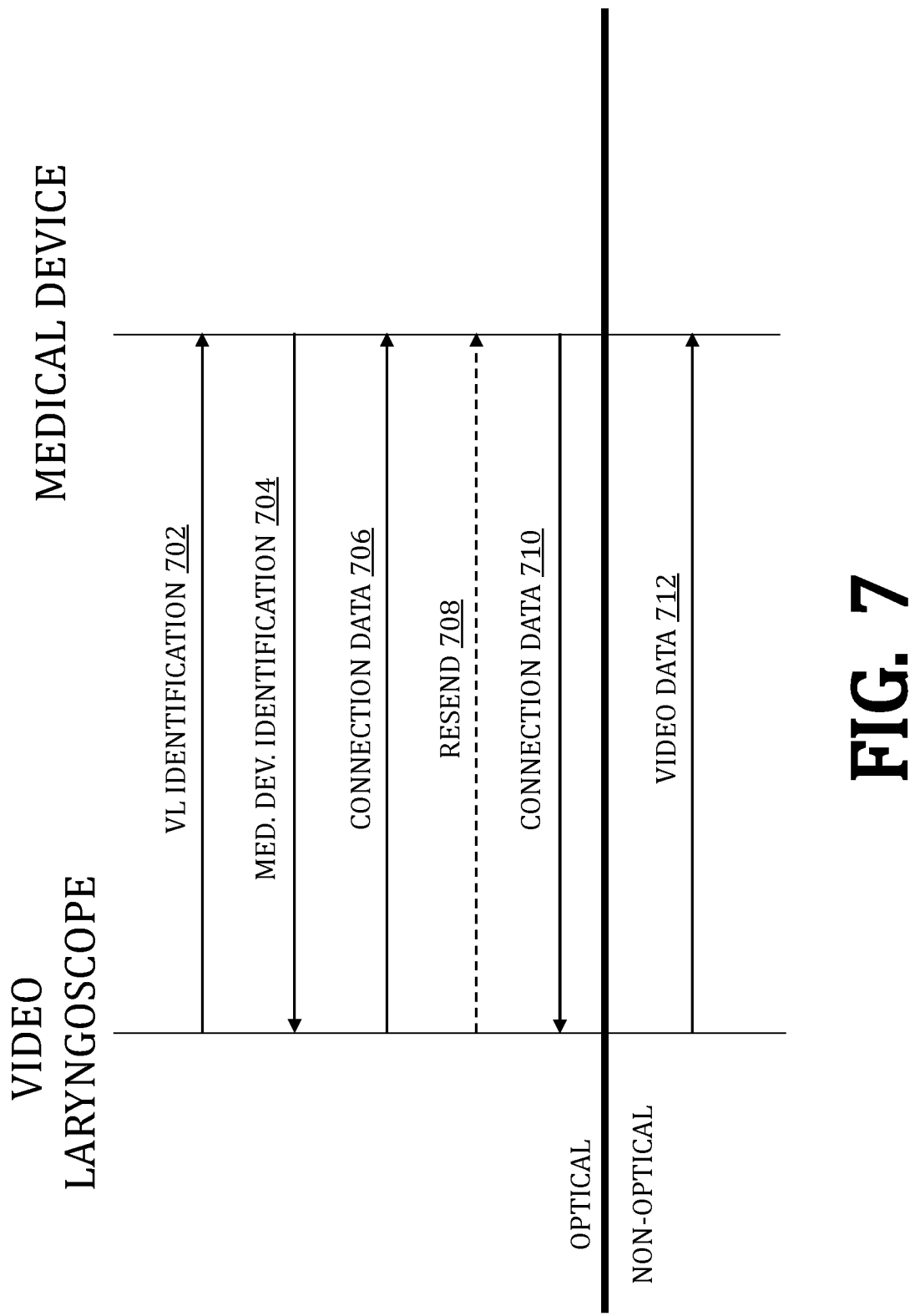
FIG. 7 depicts a communication diagram illustrating example pairing communications between a video laryngoscope and a medical device.

While the example medical devices discussed in FIGS. 6-7 are anesthesia machines and defibrillators, the concepts apply to other medical devices as well. For any of these devices, the medical device may include a video-laryngoscope-pairing PCBA and a primary-function PCBA. The components of the video-laryngoscope-pairing PCBA facilitate the pairing of the video laryngoscope, and the components of the primary-function PCBA perform the primary medical functions of the medical device (e.g., the medical purpose for the medical device).

In an embodiment, the pairing PCBA is integrated into a variety of different medical devices with different primary functions, from different manufacturers. For instance, the pairing PCBA may be configured to be integrated into different types of devices. A single video laryngoscope handle can travel between rooms and automatically connect to all of these different external medical devices without further input from a user and without requiring the devices to be previously paired to the video laryngoscope. Accordingly, the video laryngoscope is effectively device agnostic as it can connect to multiple different types of medical devices, even devices from different manufacturers or producers.

The pairing PCBA may also provide or expose an application programming interface (API) that allows the components of the primary function PCBA interface with the components of the pairing PCBA and retrieve data from, sent data to, or exchange data with the components of the pairing PCBA. For instance, as discussed above, the pairing PCBA may be able to be incorporated into multiple different types of devices. Accordingly, when the pairing PCBA is installed in the medical device and connected to the primary-function PCBA, the different types of the primary-function PCBAs can all communicate with the pairing PCBA via the API. For example, the components of the primary function PCBA may provide data about the connections or pairing to the pairing PCBA via the API. The components of the primary function PCBA may also configure some settings or features of the pairing PCBA components, such as a clock or time setting to facilitate synchronization.

The pairing PCBA and the primary-function PCBA may also take different forms that may not be fully separate PCBAs. For instance, the pairing functions may be performed by a first set of integrated or non-removable hardware, circuitry, and/or components. Similarly, the primary functions of the medical device may be performed by a second set of integrated or non-removable hardware, circuitry, and/or components.

FIG. 7 depicts a communication diagram illustrating example pairing communications between a video laryngoscope and a medical device, such as an anesthesia machine or a defibrillator. In the example depicted, when the video laryngoscope is powered on, the video laryngoscope may automatically emit an optical signal with video laryngoscope identification data 702. The video laryngoscope identification data 702 identifies the video laryngoscope and may indicate to the medical device that an active video laryngoscope is present within the room. The video laryngoscope identification data 702 is stored in the video laryngoscope and may static.

The medical device emits an optical signal with medical device identification data 704. The emission of the medical device identification data 704 may be triggered by the receipt of the video laryngoscope identification data 702. In other examples, the medical device may emit the medical device identification data 704 automatically when the medical device is powered on other otherwise activated.

The video laryngoscope then emits an optical signal with connection data 706 for facilitating communication in a non-optical band, such as pairing data for establishing a non-optical pairing or communication session. In an example where the non-optical band is WiFi-based, the connection data 706 may include a Service Set Identifier (SSID) and pre-shared key (PSK) data for a wireless (e.g., WiFi) network. In combination with sending the connection data 706, the video laryngoscope may also open or begin opening a wireless access point that corresponds to the connection data (e.g., an access point with the SSID and accessible with the PSK). The emission of the connection data 706 may be triggered based on the receipt of the medical device identification data 704.

In some examples, the video laryngoscope may resend the connection data 706, such as when a response is not received from the medical device within a set duration. For instance, an optical signal may be emitted with resent connection data 708. The connection data 706 may be resent a set number of times, such as two or three times.

When the connection data 706 is received by the medical device, the medical device sends the connection data back to the video laryngoscope. For instance, the wireless hub emits an optical signal with the reflected or returned connection data 710. The returned connection data 710 serves as a check that the medical device did in fact receive the connection data 706 and that the medical device is configured to process the data that is optically transmitted from the video laryngoscope. The returned connection data 710 may also include additional authentication data for the wireless hub where such information is not already included in the medical device identification data 704. When the video laryngoscope receives the returned connection data 710, the video laryngoscope may perform authentication operations to verify or authenticate the identity of the medical device.

Once the returned connection data 710 is received (and authentication is performed), the non-optical wireless communication is established based on the connection data 710. For example, where the wireless connection is WiFi based, the access point may be established and the medical device and the video laryngoscope communicate wirelessly via the access point. Once the non-optical communication is established, the medical device may stop emitting optical signals and ignore new or subsequent optical signals.

Image or video data may then be transmitted from the video laryngoscope to the medical device via the non-optical communication connection. As discussed further herein, transmission of image data may include streaming image or video data. The transmission of image data may also include the transmission of a recording (e.g., a completed video file) from the video laryngoscope to the medical device. In some examples, data may also be sent from the medical device to the video laryngoscope via the non-optical communication connection. For instance, the medical device may communication changes in the non-optical connection, such as which port the medical device or video laryngoscope is connected.

Once the video laryngoscope is connected to the medical device, the communication protocol identified in FIG. 7 may then repeat for connections to additional or subsequent medical devices, computers, external displays, or wireless hubs. Accordingly, serial connections may be formed between the video laryngoscope and additional wireless hubs. In examples where WiFi communication is used, the access point will already have been opened by the video laryngoscope when the connection to the first wireless hub is established. Thus, for subsequent connections to additional wireless hubs, the same access point may be used, and additional Internet Protocol (IP) addresses may be used for the subsequent connections to additional wireless hubs.

FIG. 8A depicts an example method 800 of wirelessly connecting a video laryngoscope to medical devices in multiple rooms. The operations of method 800 may be performed by a video laryngoscope. For instance, the memory of the video laryngoscope may store instructions that, when executed by one or more processors or the video laryngoscope, cause one or more operations of method 800 to be performed.

At operation 802, a power-on input is received in a first room or first environment. For instance, a power button of the video laryngoscope may be pressed by a user. Based on receiving the power-on input, the video laryngoscope powers up or turns on. At operation 804, upon startup, optical signals are emitted to and/or received from one or more other devices in the first room, such as medical devices, external displays, computers, or wireless hubs.

At operation 806, a non-optical wireless connection is established with the medical device and/or other devices in the first room based the optical data that was exchanged in operation 804. The non-optical wireless connection may be established without any additional input from the user after the video laryngoscope powers on. The non-optical connection may be established using algorithms or protocols such as the one depicted in FIG. 7. For instance, no pairing codes or other confirmations may need to be provided by the medical professional performing the intubation procedure. Operations 804 and 806 may be performed without having any previously stored pre-pairing or unique connection data about the external devices to which the video laryngoscope connects. For instance, the devices have not been pre-paired prior to operations 804 and 806. In addition, operations 804 and 806 may be performed automatically without any user input other than the input to power-on the video laryngoscope in operation 802.

At operation 807, during the medical procedure, such as an intubation procedure, the camera of the video laryngoscope captures video data (e.g., a series of images). At operation 808, during or after the medical procedure is performed with the video laryngoscope, the video or image data is transmitted from the video laryngoscope to the one or more medical devices or other devices within the first room with which the video laryngoscope is connected. For example, as the image data is captured from the camera of the laryngoscope (or received from a connected external endoscope camera), the image data may be transmitted to the connected medical device or other device within the first room.

At operation 810, a power-off input is received. For instance, the power button may be again selected by the medical professional to power off the device. At operation 812, upon receiving the power-off input, the video laryngoscope may erase the current pairing or connection data to prevent subsequent connections to the devices in the first room without having to perform the optical pairing processes discussed herein. At operation 813, the video laryngoscope performs a power-off sequence and the device powers off. In some examples, the power-off sequence may include a final transmission of the video data that has not been previously transmitted to the connected device(s). For instance, a local recording of the video data may be generated on the video laryngoscope, and that recording may not be transmitted until the power-off input is received and the power-off sequence is performed.

At operation 814, with the video laryngoscope in a second room or second environment, a power-on input is received. At operation 816, upon startup, optical signals are emitted to and/or received from one or more other devices in the second room, such as medical devices, external displays, computers, or wireless hubs that are different from the devices that are in the first room.

At operation 818, a non-optical wireless connection is established with the medical device(s) and/or other devices in the second room based the optical data that was exchanged in operation 816. The non-optical wireless connection may be established without any additional input from the user after the video laryngoscope powers on in the second room. The non-optical connection may be established using algorithms or protocols such as the one depicted in FIG. 7. For instance, no pairing codes or other confirmations may need to be provided by the medical professional performing the intubation procedure. Of note, at operation 818, the non-optical connection is not reestablished with any of the devices in the first room.

At operation 819, during the medical procedure, such as an intubation procedure, the camera of the video laryngoscope captures video data (e.g., a series of images). At operation 820, during or after the medical procedure performed with the video laryngoscope in the second room, the video or image data is transmitted from the video laryngoscope to the one or more medical devices or other devices within the second room with which the video laryngoscope is connected. For example, as the image data is captured from the camera of the laryngoscope (or received from a connected endoscope camera) during the procedure in the second room, the image data may be transmitted to the connected medical device or other device within the second room.

At operation 822, a power-off input is received. For instance, the power button may be again selected by the medical professional to power off the device. At operation 824, upon receiving the power-off input, the video laryngoscope may erase the current pairing or connection data to prevent subsequent connections to the devices in the second room without having to perform the optical pairing processes discussed herein. At operation 826, the video laryngoscope performs a power-off sequence and the device powers off. In some examples, the power-off sequence may include a final transmission of the video data that has not been previously transmitted to the connected device(s). For instance, a local recording of the video data may be generated on the video laryngoscope during the procedure in the second room, and that recording may not be transmitted until the power-off input is received and the power-off sequence is performed.

Unlike other pairing protocols that may automatically restore prior connections (e.g., some Bluetooth or WiFi protocols) when the devices are brought in proximity to one another, the present technology may prevent such restoration of previous connections to avoid connecting to a device in a different room. For example, the automated connection of the present technology initiates optical communication even to connect to a device to which the video laryngoscope had been previously connected. Even though optical portion of the connection protocol is performed each time the video laryngoscope is powered on, the automatic establishment still may occur with a single press of the power button, which results in a one-touch connection between the video laryngoscope and the other devices without any additional interaction required from the medical professional. In some examples, recording of the acquired images may also automatically begin upon powering the video laryngoscope. As such, the single press or touch of the power button may result in automatic connection to other devices along with video recording and/or streaming without additional interaction with the medical professional.

Figure 8B:
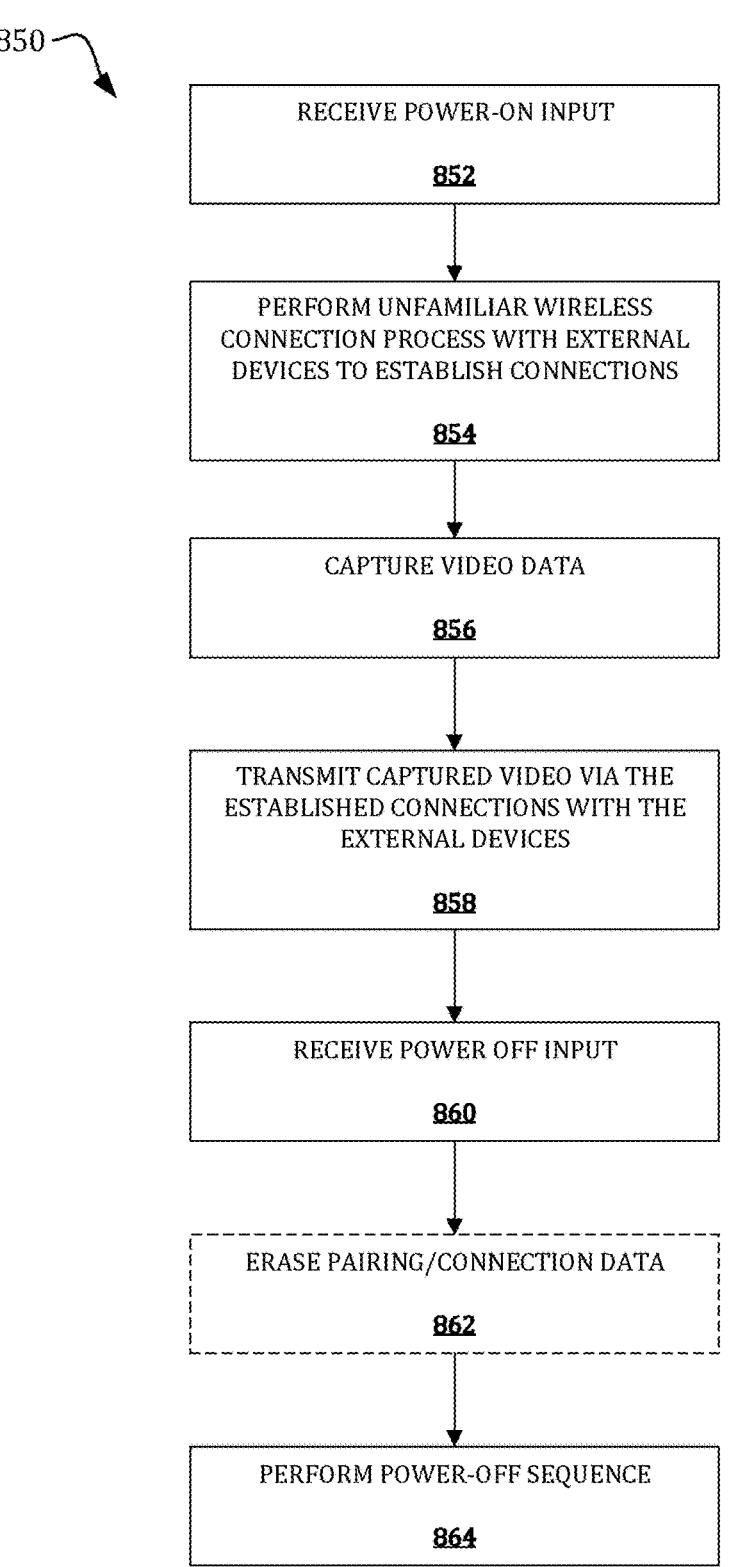
FIG. 8B depicts an example method for performing an unfamiliar wireless connection process to connect a video laryngoscope to external devices.

FIG. 8B depicts an example method 850 for performing an unfamiliar wireless connection process to connect a video laryngoscope to external devices. The operations of method 850 may be performed by a video laryngoscope. For instance, the memory of the video laryngoscope may store instructions that, when executed by one or more processors or the video laryngoscope, cause one or more operations of method 800 to be performed.

At operation 852, a power-on input is received by the video laryngoscope. Operation 852 may be the same or similar as operation 802 in method 800 described above. At operation 854, an unfamiliar wireless connection process is performed with one or more external devices (e.g., medical devices, headless hubs, external displays) within the room, theater, or environment to establish a connection with the one or more external devices. Where there are multiple external devices available, the unfamiliar wireless connection process may be performed for each of the external devices to establish a wireless connection with each of the wireless connection devices. The unfamiliar wireless connection process may performed and completed without any user input being received after the power-on input is received at operation 852. As used herein, performing an unfamiliar wireless connection process means establishing a wireless connection between the video laryngoscope and an external device for which the video laryngoscope does not have unique connection information for establishing the wireless connection with the particular external device. For instance, the external device may be a device to which the video laryngoscope has never been previously connected (e.g., an "unfamiliar" external device). Or, as discussed further herein, the external device may a device to which the video laryngoscope has been previously connected, but the video laryngoscope has deleted or erased the prior connection data-thus resulting the external device again being considered unfamiliar. The video laryngoscope may also not store (prior to the unfamiliar connection process) any pre-pairing information or connection information that would allow for pairing or connection to the external device without performing the unfamiliar wireless connection process. By performing unfamiliar wireless connection, the video laryngoscope is able to establish a wireless connection with these unfamiliar external devices without any input from the user to establish that connection.

In some examples, performing the unfamiliar wireless connection process may include performing the optical pairing/connection processes discussed above, such as in FIGS. 7 and 8A. In other examples, performing the unfamiliar wireless connection process may include using other methods to establish the wireless connection between the video laryngoscope and the wireless device. For instance, the video laryngoscope may have a first video-laryngoscope transceiver and a second video-laryngoscope transceiver. The external device (e.g., medical device) may also have a first device transceiver and a second device transceiver. The first device transceiver and a second device transceiver may integrated into the external device (e.g., non-removable).

The performing the unfamiliar wireless connection process may include exchanging (e.g., transmitting and/or receiving) wireless signals by the first video-laryngoscope transceiver and the first device transceiver. Then, based on the data in those wireless signals, a wireless connection is established between second video-laryngoscope transceiver and the second device transceiver. The data in the first wireless signals exchanged signals by the first video-laryngoscope transceiver and the first device transceiver may include unique connection information for the particular external device to allow for pairing/connecting with that particular external device.

The first video-laryngoscope transceiver and the first device transceiver may use (e.g., communicate on) a first type of wireless signal, and the second video-laryngoscope transceiver and the second device transceiver may utilize a second type of wireless signal that is different from the first type of wireless signal. For instance, the first type of wireless signal may be an optical signal as discussed above. In other examples, the first type of wireless signal may be a short-range wireless signal or a wireless signal within limited power, which may be non-optical.

By using a short-range wireless signal or power-limited wireless signal, communication with external devices in other rooms or environments may also be limited. As a result, the video laryngoscope is more likely to pair or connect only with external devices that are within proximity to the video laryngoscope (e.g., in the same room). In addition, where the first type of wireless signal is configured to be usefully detectable within a few feet of the video laryngoscope, the connections are limited to devices within that particular range. Such a limitation or feature may be useful in environments where there are multiple patients and devices in use within the same room, such as an emergency room with multiple beds. In such environments, multiple video laryngoscopes may be used and the connections to external devices may be limited to the external devices most proximate the patient for which the intubation procedure is being performed.

The second type of wireless signal may be the same or similar to the non-optical wireless signals discussed above, such as with respect to FIGS. 7 and 8A. For instance, the second type of wireless signal may be a Bluetooth, WiFi, or similar type of signal.

At operation 856, the video laryngoscope captured images in the form of video data. At operation 858, the captured video data is transmitted to the external devices via the connections established in operation 854. For instance, the captured video data may be transmitted via the second type of wireless signal. As an example, the captured video data may be transmitted from the second video-laryngoscope transceiver and received by the second device transceiver.

At operation 860, a power off input is received. Based on receiving the power-off input, the pairing/connection data generated or received in operation 854 may be erased or deleted. For example, unique connection information received for the particular external devices may be erased. Accordingly, the connected external devices become again unfamiliar to the video laryngoscope. At operation 864, a power-off sequence may be performed and the video laryngoscope powers off. Operations 860, 862, and 864 may be substantially similar to or the same as operations 810, 812, and 813 of method 800 in FIG. 8A.

FIG. 9 depicts an example method 900 of wirelessly receiving and processing video data received from a video laryngoscope. The method 900 may be performed by a medical device, such as a defibrillator, anesthesia machine, ventilator, patient monitor, medical imaging equipment, ECG machines, IV pump, and the like. For instance, the medical device may include an optical transceiver (or transmitter and/or receiver), a wireless communication device, one or more processors, and memory storing instructions that when executed by the one or more processors causes the medical device to perform one or more operations of method 900.

At operation 902, an optical signal from the video laryngoscope is detected. Based on the optical signal from the video laryngoscope, a non-optical connection with the video laryngoscope is established based on the data in the optical signal at operation 904. The non-optical connection may be established using algorithms or protocols such as those depicted in FIGS. 7 and 8. At operation 906, video data is received from the video laryngoscope via the non-optical connection.

From operation 906, the method 900 may flow to operation 908, operation 910, or operation 916. At operation 908, the received video data is stored in memory of the medical device. At operation 916, a video stream of the video data is displayed on a display of the medical device. The video data may be both stored and displayed in some examples.

At operation 910, the video data from the video laryngoscope may be synchronized with additional data from the medical device. For instance, the medical device may capture additional data about the patient and/or the operations of the medical device that may be time stamped or in a time series. As an example, the medical device may include patient monitoring sensors that track physiological parameters of the patient. These physiological parameters may be synchronized with the video data. At operation 912, a data package including the data captured from the medical device and the video data from the video laryngoscope may be generated. At operation 914, the generated data package may then be transmitted over a network connection to a medical database that may be in a device that is located remotely from the medical device.

The methods discussed herein include various steps represented by blocks in flow diagrams. It should be noted that at least some steps may be performed as an automated procedure by one or more components of a system. Although the flow diagrams may illustrates the steps in a certain sequence, it should be understood that the steps may be performed in any suitable order and certain steps may be carried out simultaneously, where appropriate. Additionally, steps may be added to or omitted from of the methods.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A system for transmitting video laryngoscope images, comprising:

a plurality of external devices including a medical device with a display screen; and a video laryngoscope comprising a camera, an optical transceiver, a non-optical wireless transmitter, a processor, and memory storing instructions that, when executed by the processor, cause the video laryngoscope to perform operations comprising:

automatically, upon startup and without further user input, performing an unfamiliar wireless connection process for each of the plurality of external devices located within a first room with the video laryngoscope to establish a wireless connection to each of the plurality of external devices;

transmitting, via the established wireless connections, images captured by the camera to the plurality of external devices;

receiving a power-off input;

powering off the video laryngoscope in response to the power-off input;

receiving a power-on input in a second room different from the first room;

based on receiving the power-on input, detecting an optical signal from a medical device in the second room; and based on the optical signal from a medical device in the second room, establishing a non-optical connection with the medical device in the second room but not with any of the plurality of external devices located in the first room.

2. The system of claim 1, wherein the medical device in the second room is one of a defibrillator, an anesthesia machine, a multi-parameter monitor, a medical imaging device, an electrocardiogram (ECG) machine, or an intravenous (IV) pump.

3. The system of claim 1, wherein the medical device displays, on the display, the images transmitted by the video laryngoscope.

4. The system of claim 1, wherein performing the unfamiliar wireless connection process comprises:

exchanging wireless signals, having a first wireless signal type, between the video laryngoscope and the each of the plurality of external devices; and wherein the wireless connection is of a second wireless signal type, and establishing the wireless connection is based on data in exchanged wireless signals.

5. The system of claim 4, wherein:

the video laryngoscope comprises a first transceiver that communicates on the first wireless signal type and a second transceiver that communicates on the second wireless signal type; and each of the plurality of external devices includes a first transceiver that communicates on the first wireless signal type and a second transceiver that communicates on the second wireless signal type.

6. The system of claim 4, wherein the wireless signals are optical signals, and the established wireless connections are non-optical connections.

7. The system of claim 6, wherein the unfamiliar wireless connection process comprises, upon startup, emitting an optical signal that encodes identification information for the video laryngoscope.

8. The system of claim 6, wherein the medical device comprises an optical window in a housing of the medical device and an optical transceiver positioned behind the optical window of the medical device.

9. A system for transmitting video laryngoscope images, comprising:

a medical device comprising:

a first optical transceiver that detects and emits optical signals;

a first non-optical wireless transceiver that transmits and receives non-optical data signals;

a display;

a first memory; and a first processor;

a headless hub comprising:

a second optical transceiver that detects and emits optical signals;

a second non-optical wireless transceiver that transmits and receives non-optical data signals;

a second memory; and a second processor;

a video laryngoscope comprising:

a camera that acquires images;

a third optical transceiver that detects and emits optical signals;

a third non-optical wireless transceiver that transmits and receives non-optical data signals;

a third processor; and a third memory storing instructions that, when executed by the third processor, causes the video laryngoscope to perform operations comprising:

detect, by the third optical transceiver, a first optical signal from the first optical transceiver of the medical device;

detect, by the third optical transceiver, a second optical signal from the second optical transceiver of the headless hub;

based on data in the first optical signal, establish, by the third non-optical wireless transceiver and without prior or further user input, a first non-optical connection with the first non-optical wireless transceiver of the medical device;

based on data in the second optical signal, establish, by the third non-optical wireless transceiver and without prior or further user input, a second non-optical connection with the second non-optical wireless transceiver of the headless hub;

capture, by the camera, video data;

transmit the captured video data to the medical device via the first non-optical connection; and transmit the captured video data to the headless hub via the second non-optical connection.

10. The system of claim 9, wherein the first memory of the medical device stores instructions that, when executed by the first processor causes the medical device to perform operations comprising:

receive the transmitted video data from the video laryngoscope; and display the video data on the display.

11. The system of claim 10, wherein the first memory of the medical device stores instructions that, when executed by the first processor causes the medical device to perform operations further comprising:

generate physiological parameter data about a patient;

combine the video data and the physiological parameter data into a data package; and transmit the data package to a medical database located remotely from the medical device.

12. The system of claim 9, wherein the medical device further comprises an optical window in a housing of the medical device, and the first optical transceiver is positioned behind the optical window.

13. The system of claim 9, wherein the medical device further comprises:

a video-laryngoscope pairing printed circuit board assembly (PCBA) that includes the first processor, the first memory, the first optical transceiver, and the first non-optical wireless transceiver; and a primary-function PCBA that includes a fourth processor and a fourth memory that stores instructions for performing primary functions of the medical device.

14. A method, performed by a video laryngoscope, for transmitting image data captured by the video laryngoscope, the method comprising:

while in a first patient environment, receiving a first power-on input;

upon startup in response to the first power-on input and without requiring any further user input, detecting a first optical signal from a first medical device having a first display screen;

based on the first optical signal and without pre-pairing, establishing a first non-optical connection with the first medical device;

capturing first images by a camera of the video laryngoscope during a first medical procedure being performed in the first patient environment;

transmitting the first images to the first medical device via the first non-optical connection;

powering off the video laryngoscope;

subsequently, while in a second patient environment, receiving a second power-on input;

upon startup in response to the second power-on input, and without requiring any further user input, detecting a second optical signal from a second medical device having a second display screen, the second medical device being different from the first medical device;

based on the second optical signal and without pre-pairing, establishing a second non-optical connection with the second medical device and not the first medical device;

capturing second images by the camera of the video laryngoscope during a second medical procedure being performed in the second patient environment; and transmitting the second images to the second medical device via the second non-optical connection.

15. The method of claim 14, wherein the first medical device is one of a defibrillator, an anesthesia machine, a medical imaging device, an electrocardiogram (ECG) machine, or an intravenous (IV) pump.

16. The method of claim 14, wherein the first medical device is a defibrillator.

17. The method of claim 14, wherein the first medical device is an anesthesia machine.

18. The method of claim 14, wherein transmission of the second images to the second medical device causes a display of the second images on a display of the second medical device.

19. The method of claim 14, wherein the first patient environment is an ambulance.

20. The method of claim 14, wherein the first patient environment is a first hospital room and the second patient environment is a second hospital room.

\* \* \* \* \*